US008906618B2

(12) United States Patent
O'Keefe et al.

(10) Patent No.: US 8,906,618 B2
(45) Date of Patent: *Dec. 9, 2014

(54) APPARATUS AND METHODS FOR PARALLEL PROCESSING OF MICRO-VOLUME LIQUID REACTIONS

(75) Inventors: Matthew O'Keefe, Saratoga, CA (US); Pamela K. Foreman, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/269,118

(22) Filed: Oct. 7, 2011

(65) Prior Publication Data
US 2012/0077194 A1    Mar. 29, 2012

Related U.S. Application Data

(60) Continuation of application No. 12/582,652, filed on Oct. 20, 2009, now Pat. No. 8,053,185, which is a division of application No. 11/054,184, filed on Feb. 9, 2005, now Pat. No. 7,604,983, which is a continuation of application No. 09/935,455, filed on Aug. 22, 2001, now abandoned, which is a continuation-in-part of application No. 09/789,899, filed on Feb. 20, 2001, now abandoned.

(60) Provisional application No. 60/229,357, filed on Feb. 18, 2000.

(51) Int. Cl.
| | | |
|---|---|---|
| C12Q 1/68 | (2006.01) | |
| H01J 49/04 | (2006.01) | |
| B01F 13/00 | (2006.01) | |
| C40B 40/06 | (2006.01) | |
| B01L 3/00 | (2006.01) | |
| B01F 15/02 | (2006.01) | |
| C40B 60/14 | (2006.01) | |

(52) U.S. Cl.
CPC ......... B01F 13/0071 (2013.01); H01J 49/0418 (2013.01); B01L 2300/087 (2013.01); C40B 40/06 (2013.01); B01L 3/5088 (2013.01); B01L 2300/165 (2013.01); B01L 2300/0819 (2013.01); B01F 15/0201 (2013.01); B01F 15/0232 (2013.01); C40B 60/14 (2013.01); B01L 3/5025 (2013.01); B01J 2219/0072 (2013.01); B01J 2219/0074 (2013.01); B01L 2300/0829 (2013.01); B01F 13/0084 (2013.01); B01L 2200/0642 (2013.01); B01F 2215/0431 (2013.01); B01L 2400/0688 (2013.01); B01F 13/0059 (2013.01); B01J 2219/00722 (2013.01); B01J 2219/00317 (2013.01); B01L 3/50857 (2013.01); B01J 2219/00286 (2013.01); B01L 2300/10 (2013.01)
USPC .......... 435/6.11; 435/6.12; 435/91.2

(58) Field of Classification Search
USPC ............... 435/6.11, 6.12, 91.2, 288.4, 288.7, 435/303.1
See application file for complete search history.

(56) References Cited

U.S. PATENT DOCUMENTS

| | | |
|---|---|---|
| 1,236,137 A | 8/1917 | Bastow |
| 2,745,001 A | 5/1956 | Guth |
| 2,771,398 A | 11/1956 | Snyder |
| 3,043,669 A | 7/1962 | Charles |
| 3,170,980 A | 2/1965 | Pritchard |
| 3,252,331 A | 5/1966 | Lancaster |
| 3,768,974 A | 10/1973 | Storm |
| 3,770,383 A | 11/1973 | Price |
| 3,864,512 A | 2/1975 | Meadow |
| 3,873,268 A | 3/1975 | Mckie, Jr. |
| 3,894,512 A | 7/1975 | Ohno et al. |
| 3,997,396 A | 12/1976 | Delente |
| 4,007,010 A | 2/1977 | Woodbridge, III |
| 4,065,263 A | 12/1977 | Woodbridge, III |
| 4,088,448 A | 5/1978 | Liljy et al. |
| 4,110,165 A | 8/1978 | Cole et al. |
| 4,111,754 A | 9/1978 | Park |
| 4,234,316 A | 11/1980 | Hevey |
| 4,273,877 A | 6/1981 | Anagnostopoulos |
| 4,415,732 A | 11/1983 | Caruthers et al. |
| 4,446,239 A | 5/1984 | Tsuji et al. |
| 4,453,805 A | 6/1984 | Ashkin et al. |
| 4,458,066 A | 7/1984 | Caruthers et al. |

(Continued)

FOREIGN PATENT DOCUMENTS

| | | |
|---|---|---|
| EP | 0506993 | 10/1992 |
| JP | 63107057 | 5/1988 |

(Continued)

OTHER PUBLICATIONS

Adlercreutz et al., "Oxygen Supply to Immobilized Cells", Eur. J. Appl. Biotechnolow, 1982, 16, 165-70.

(Continued)

*Primary Examiner* — Willaim H Beisner
(74) *Attorney, Agent, or Firm* — Edward J. Baba; Bozicevic, Field & Francis LLP

(57) ABSTRACT

Disclosed herein are apparatuses and methods for conducting multiple simultaneous micro-volume chemical and biochemical reactions in an array format. In one embodiment, the format comprises an array of microholes in a substrate. Besides serving as an ordered array of sample chambers allowing the performance of multiple parallel reactions, the arrays can be used for reagent storage and transfer, library display, reagent synthesis, assembly of multiple identical reactions, dilution and desalting. Use of the arrays facilitates optical analysis of reactions, and allows optical analysis to be conducted in real time. Included within the invention are kits comprising a microhole apparatus and a reaction component of the method(s) to be carried out in the apparatus.

18 Claims, 6 Drawing Sheets

(56) References Cited

U.S. PATENT DOCUMENTS

| | | |
|---|---|---|
| 4,493,815 A | 1/1985 | Fernwood et al. |
| 4,500,707 A | 2/1985 | Caruthers et al. |
| 4,562,045 A | 12/1985 | Murata et al. |
| 4,562,871 A | 1/1986 | Astle |
| 4,613,573 A | 9/1986 | Shibayama et al. |
| 4,626,509 A | 12/1986 | Lyman |
| 4,663,163 A | 5/1987 | Hou et al. |
| 4,682,890 A | 7/1987 | de Macario et al. |
| 4,682,891 A | 7/1987 | de Macario et al. |
| 4,683,195 A | 7/1987 | Mullis et al. |
| 4,683,202 A | 7/1987 | Mullis |
| 4,701,304 A | 10/1987 | Horn et al. |
| 4,734,192 A | 3/1988 | Champion et al. |
| 4,761,378 A | 8/1988 | Godsey |
| 4,828,386 A | 5/1989 | Matkovich et al. |
| 4,834,946 A | 5/1989 | Levin |
| 4,861,448 A | 8/1989 | Cantor et al. |
| 4,861,722 A | 8/1989 | Sana et al. |
| 4,893,886 A | 1/1990 | Ashkin et al. |
| 4,932,806 A | 6/1990 | Eklund et al. |
| 4,965,188 A | 10/1990 | Mullis et al. |
| 4,973,679 A | 11/1990 | Caruthers et al. |
| 4,990,459 A | 2/1991 | Maeda et al. |
| 5,000,921 A | 3/1991 | Hanaway et al. |
| 5,009,846 A | 4/1991 | Gavet et al. |
| 5,038,852 A | 8/1991 | Johnson et al. |
| 5,047,215 A | 9/1991 | Manns |
| 5,100,627 A | 3/1992 | Buican et al. |
| 5,108,704 A | 4/1992 | Bowers et al. |
| 5,108,926 A | 4/1992 | Klebe |
| 5,152,060 A | 10/1992 | Schubert et al. |
| 5,153,319 A | 10/1992 | Caruthers et al. |
| 5,175,209 A | 12/1992 | Beattie et al. |
| 5,192,980 A | 3/1993 | Dixon et al. |
| 5,210,021 A | 5/1993 | Goodwin, Jr. |
| 5,215,593 A | 6/1993 | Nojo et al. |
| 5,219,727 A | 6/1993 | Wang et al. |
| 5,229,163 A | 7/1993 | Fox |
| 5,234,665 A | 8/1993 | Ohta et al. |
| 5,234,666 A | 8/1993 | Suzuki et al. |
| 5,242,974 A | 9/1993 | Holmes |
| 5,262,128 A | 11/1993 | Leighton et al. |
| 5,284,753 A | 2/1994 | Goodwin |
| 5,290,705 A | 3/1994 | Davis |
| 5,310,652 A | 5/1994 | Gelfand et al. |
| 5,322,019 A | 6/1994 | Hyland |
| 5,322,770 A | 6/1994 | Gelfand |
| 5,333,675 A | 8/1994 | Mullis et al. |
| 5,373,803 A | 12/1994 | Noguchi et al. |
| 5,374,525 A | 12/1994 | Lalouel et al. |
| 5,382,985 A | 1/1995 | Becker et al. |
| 5,407,800 A | 4/1995 | Gelfand et al. |
| 5,411,876 A | 5/1995 | Bloch et al. |
| 5,427,908 A | 6/1995 | Dower et al. |
| 5,433,975 A | 7/1995 | Roberts et al. |
| 5,445,934 A | 8/1995 | Fodor et al. |
| 5,453,252 A | 9/1995 | Truett |
| 5,455,008 A | 10/1995 | Earley et al. |
| 5,466,583 A | 11/1995 | Thomson et al. |
| 5,475,610 A | 12/1995 | Atwood et al. |
| 5,476,744 A | 12/1995 | Anno et al. |
| 5,476,774 A | 12/1995 | Wang et al. |
| 5,491,083 A | 2/1996 | Arentzen et al. |
| 5,492,806 A | 2/1996 | Drmanac et al. |
| 5,504,007 A | 4/1996 | Haynes |
| 5,506,141 A | 4/1996 | Weinreb et al. |
| 5,508,197 A | 4/1996 | Hansen et al. |
| 5,508,200 A | 4/1996 | Tiffany et al. |
| 5,510,270 A | 4/1996 | Fodor et al. |
| 5,519,218 A | 5/1996 | Chanq |
| 5,525,464 A | 6/1996 | Drmanac et al. |
| 5,538,848 A | 7/1996 | Livak et al. |
| 5,554,339 A | 9/1996 | Cozzette et al. |
| 5,560,811 A | 10/1996 | Briggs et al. |
| 5,561,058 A | 10/1996 | Gelfand et al. |
| 5,561,071 A | 10/1996 | Hollenberg et al. |
| 5,576,220 A | 11/1996 | Hudson et al. |
| 5,580,717 A | 12/1996 | Dower et al. |
| 5,585,275 A | 12/1996 | Hudson et al. |
| 5,593,839 A | 1/1997 | Hubbell et al. |
| 5,599,664 A | 2/1997 | Schwartz |
| 5,602,756 A | 2/1997 | Atwood et al. |
| 5,605,662 A | 2/1997 | Heller et al. |
| 5,609,828 A | 3/1997 | O'Bear et al. |
| 5,621,094 A | 4/1997 | Roser et al. |
| 5,632,957 A | 5/1997 | Heller et al. |
| 5,641,391 A | 6/1997 | Hunter et al. |
| 5,641,864 A | 6/1997 | Gelfand |
| 5,656,493 A | 8/1997 | Mullis et al. |
| 5,667,972 A | 9/1997 | Drmanac et al. |
| 5,670,329 A | 9/1997 | Oberhardt |
| 5,710,381 A | 1/1998 | Atwood et al. |
| 5,720,923 A | 2/1998 | Haff et al. |
| 5,722,370 A | 3/1998 | Koike et al. |
| 5,744,101 A | 4/1998 | Fodor et al. |
| 5,763,263 A | 6/1998 | Dehlinger |
| 5,770,440 A | 6/1998 | Berndt |
| 5,770,860 A | 6/1998 | Franzen et al. |
| 5,773,238 A | 6/1998 | Shukla |
| 5,780,233 A | 7/1998 | Guo et al. |
| 5,785,926 A | 7/1998 | Seubert et al. |
| 5,786,226 A | 7/1998 | Boeker et al. |
| 5,795,748 A | 8/1998 | Cottingham |
| 5,807,522 A | 9/1998 | Brown et al. |
| 5,840,862 A | 11/1998 | Bensimon et al. |
| 5,843,767 A | 12/1998 | Beattie |
| 5,849,598 A | 12/1998 | Wilson et al. |
| 5,856,100 A | 1/1999 | Hayashizaki et al. |
| 5,871,908 A | 2/1999 | Henco et al. |
| 5,879,632 A | 3/1999 | Demers |
| 5,888,723 A | 3/1999 | Sutton et al. |
| 5,897,842 A | 4/1999 | Dunn et al. |
| 5,906,683 A | 5/1999 | Chen et al. |
| 5,910,287 A | 6/1999 | Cassin et al. |
| 5,922,604 A | 7/1999 | Stapleton et al. |
| 5,928,907 A | 7/1999 | Woudenberg et al. |
| 5,929,208 A | 7/1999 | Heller et al. |
| 5,942,432 A | 8/1999 | Smith et al. |
| 5,944,652 A | 8/1999 | Miller et al. |
| 5,955,377 A | 9/1999 | Maul et al. |
| 5,958,345 A | 9/1999 | Turner et al. |
| 5,962,316 A | 10/1999 | Beach et al. |
| 5,985,214 A | 11/1999 | Stylli et al. |
| 5,994,056 A | 11/1999 | Hiquchi |
| 6,001,586 A | 12/1999 | Schellenberger |
| 6,004,744 A | 12/1999 | Goelet et al. |
| 6,015,880 A | 1/2000 | Baldeschwieler et al. |
| 6,020,141 A | 2/2000 | Pantoliano et al. |
| 6,024,925 A | 2/2000 | Little et al. |
| 6,027,873 A | 2/2000 | Schellenberger et al. |
| 6,060,240 A | 5/2000 | Kamb et al. |
| 6,071,702 A | 6/2000 | Yamamoto et al. |
| 6,071,748 A | 6/2000 | Modlin et al. |
| 6,083,682 A | 7/2000 | Campbell et al. |
| 6,083,763 A | 7/2000 | Balch |
| 6,086,825 A | 7/2000 | Sundberg et al. |
| 6,088,100 A | 7/2000 | Brenan et al. |
| 6,090,251 A | 7/2000 | Sundberg et al. |
| 6,103,199 A | 8/2000 | Bjornson et al. |
| 6,103,479 A | 8/2000 | Taylor |
| 6,107,059 A | 8/2000 | Hart |
| 6,121,048 A | 9/2000 | Zaffaroni et al. |
| 6,136,566 A | 10/2000 | Sands et al. |
| 6,136,592 A | 10/2000 | Leighton |
| H001919 H | 11/2000 | Caspar et al. |
| 6,147,198 A | 11/2000 | Schwartz |
| 6,149,815 A | 11/2000 | Sauter |
| 6,174,670 B1 | 1/2001 | Wittwer et al. |
| 6,197,563 B1 | 3/2001 | Erlich et al. |
| 6,235,473 B1 | 5/2001 | Friedman et al. |
| 6,245,505 B1 | 6/2001 | Todd et al. |
| 6,251,343 B1 | 6/2001 | Dubrow et al. |
| 6,271,024 B1 | 8/2001 | Sve et al. |
| 6,284,113 B1 | 9/2001 | Bjornson et al. |

(56) References Cited

U.S. PATENT DOCUMENTS

| | | |
|---|---|---|
| 6,296,702 B1 | 10/2001 | Bryning et al. |
| 6,306,578 B1 | 10/2001 | Schellenberger et al. |
| 6,309,600 B1 | 10/2001 | Hunter |
| 6,309,828 B1 | 10/2001 | Schleifer et al. |
| 6,312,103 B1 | 11/2001 | Haluzak |
| 6,337,435 B1 | 1/2002 | Chu et al. |
| 6,353,774 B1 | 3/2002 | Goldenberg et al. |
| 6,376,256 B1 | 4/2002 | Dunnington et al. |
| 6,387,331 B1 | 5/2002 | Hunter |
| 6,391,559 B1 | 5/2002 | Brown et al. |
| 6,399,396 B1 | 6/2002 | Bass |
| 6,399,952 B1 | 6/2002 | Maher et al. |
| 6,404,166 B1 | 6/2002 | Puchianu et al. |
| 6,406,869 B1 | 6/2002 | Glickman et al. |
| 6,410,331 B1 | 6/2002 | Schultz et al. |
| 6,429,025 B1 | 8/2002 | Parce et al. |
| 6,436,632 B2 | 8/2002 | Schellenberger et al. |
| 6,454,924 B2 | 9/2002 | Jedrzejewski et al. |
| 6,485,690 B1 | 11/2002 | Pfost et al. |
| 6,485,944 B1 | 11/2002 | Church et al. |
| 6,495,104 B1 | 12/2002 | Unno et al. |
| 6,496,369 B2 | 12/2002 | Nakamura |
| 6,503,757 B1 | 1/2003 | Chow |
| 6,514,750 B2 | 2/2003 | Bordenkircher et al. |
| 6,544,737 B1 | 4/2003 | Blumenfeld et al. |
| 6,565,813 B1 | 5/2003 | Garyantes |
| 6,572,828 B1 | 6/2003 | Potyrailo et al. |
| 6,576,478 B1 | 6/2003 | Wagner et al. |
| 6,579,358 B2 | 6/2003 | Delucas et al. |
| 6,582,914 B1 | 6/2003 | Caldwell et al. |
| 6,630,835 B2 | 10/2003 | Cheng et al. |
| 6,638,761 B2 | 10/2003 | Shin et al. |
| 6,642,000 B1 | 11/2003 | Strizhkov et al. |
| 6,649,402 B2 | 11/2003 | Van der Weide et al. |
| 6,664,044 B1 | 12/2003 | Sato et al. |
| 6,677,151 B2 | 1/2004 | Sandell |
| 6,682,702 B2 | 1/2004 | Barth et al. |
| 6,689,323 B2 | 2/2004 | Fisher et al. |
| 6,703,236 B2 | 3/2004 | Atwood |
| 6,706,538 B1 | 3/2004 | Karg et al. |
| 6,713,309 B1 | 3/2004 | Anderson et al. |
| 6,716,629 B2 | 4/2004 | Hess et al. |
| 6,730,883 B2 | 5/2004 | Brown et al. |
| 6,737,026 B1 | 5/2004 | Berqh et al. |
| 6,743,633 B1 | 6/2004 | Hunter |
| 6,812,030 B2 | 11/2004 | Ozbal et al. |
| 6,821,486 B1 | 11/2004 | Akporiaye et al. |
| 6,827,831 B1 | 12/2004 | Chow et al. |
| 6,841,663 B2 | 1/2005 | Lefkowitz et al. |
| 6,844,161 B2 | 1/2005 | Siani et al. |
| 6,848,462 B2 | 2/2005 | Covinqton et al. |
| 6,878,554 B1 | 4/2005 | Schermer et al. |
| 6,893,877 B2 | 5/2005 | Hunter et al. |
| 7,133,726 B1 | 11/2006 | Atwood et al. |
| 7,223,363 B2 | 5/2007 | McNeely et al. |
| 7,300,798 B2 | 11/2007 | Perbost et al. |
| 7,332,271 B2 | 2/2008 | O'Keefe et al. |
| 7,390,457 B2 | 6/2008 | Schembri |
| 7,604,983 B2 | 10/2009 | O'Keefe et al. |
| 7,833,719 B2 | 11/2010 | O'Keefe et al. |
| 8,053,185 B2 | 11/2011 | O'Keefe et al. |
| 2001/0046702 A1 | 11/2001 | Schembri |
| 2001/0053334 A1 | 12/2001 | Chen et al. |
| 2001/0055765 A1 | 12/2001 | O'Keefe et al. |
| 2002/0001544 A1 | 1/2002 | Hess et al. |
| 2002/0001546 A1 | 1/2002 | Hunter et al. |
| 2002/0003177 A1 | 1/2002 | O'Connor et al. |
| 2002/0015994 A1 | 2/2002 | Schellenberger et al. |
| 2002/0049196 A1 | 4/2002 | Carpino et al. |
| 2002/0072096 A1 | 6/2002 | O'Keefe et al. |
| 2002/0094533 A1 | 7/2002 | Hess et al. |
| 2002/0110900 A1 | 8/2002 | Jovanovich et al. |
| 2002/0119578 A1 | 8/2002 | Zaffaroni et al. |
| 2002/0151040 A1 | 10/2002 | O'Keefe et al. |
| 2002/0176804 A1 | 11/2002 | Strand et al. |
| 2002/0192716 A1 | 12/2002 | Schellenberger et al. |
| 2003/0003036 A1 | 1/2003 | Rouleau et al. |
| 2003/0039585 A1 | 2/2003 | Freeman |
| 2003/0064507 A1 | 4/2003 | Gallagher et al. |
| 2003/0080087 A1 | 5/2003 | Stelzle |
| 2003/0108726 A1 | 6/2003 | Schembri et al. |
| 2003/0119042 A1 | 6/2003 | Franco De Sarabia Rosado et al. |
| 2003/0124716 A1 | 7/2003 | Hess et al. |
| 2003/0170610 A1 | 9/2003 | Cima et al. |
| 2003/0180807 A1 | 9/2003 | Hess et al. |
| 2003/0186350 A1 | 10/2003 | Newell |
| 2003/0207099 A1 | 11/2003 | Gillmor et al. |
| 2003/0219716 A1 | 11/2003 | Avdeef et al. |
| 2004/0023223 A1 | 2/2004 | Thompson et al. |
| 2004/0037748 A1 | 2/2004 | Hasan et al. |
| 2004/0109793 A1 | 6/2004 | McNeely et al. |
| 2004/0132040 A1 | 7/2004 | Hamill |
| 2004/0141880 A1 | 7/2004 | Handler et al. |
| 2004/0171166 A1 | 9/2004 | Hunter |
| 2004/0191924 A1 | 9/2004 | Hunter et al. |
| 2004/0208792 A1 | 10/2004 | Linton et al. |
| 2004/0209303 A1 | 10/2004 | Martin |
| 2004/0235005 A1 | 11/2004 | Friedlander et al. |
| 2004/0241636 A1 | 12/2004 | Michnick et al. |
| 2005/0059074 A1 | 3/2005 | Schellenberger et al. |
| 2005/0079105 A1 | 4/2005 | Hunter et al. |
| 2005/0118073 A1 | 6/2005 | Facer et al. |
| 2005/0130213 A1 | 6/2005 | Morrison |
| 2005/0148066 A1 | 7/2005 | O'Keefe et al. |
| 2005/0214173 A1 | 9/2005 | Facer et al. |
| 2005/0266582 A1 | 12/2005 | Modlin et al. |
| 2006/0057209 A1 | 3/2006 | Chapman et al. |
| 2006/0105433 A1 | 5/2006 | Bickmore et al. |
| 2006/0183171 A1 | 8/2006 | Schellenberger et al. |
| 2006/0194108 A1 | 8/2006 | Drews et al. |
| 2008/0108112 A1 | 5/2008 | O'Keefe et al. |

FOREIGN PATENT DOCUMENTS

| | | |
|---|---|---|
| JP | 11/061498 | 3/1999 |
| JP | 2000/28623 | 1/2000 |
| JP | 2000/88863 | 3/2000 |
| JP | 2000/287670 | 10/2000 |
| JP | 2001/083163 | 3/2001 |
| JP | 2001/211873 | 8/2001 |
| JP | 2002/27984 | 1/2002 |
| JP | 2002/189033 | 7/2002 |
| JP | 2002/283305 | 10/2002 |
| JP | 2002/335950 | 11/2002 |
| WO | WO 91/13335 | 9/1991 |
| WO | WO 95/01559 | 1/1995 |
| WO | WO 95/11755 | 5/1995 |
| WO | WO 97/00941 | 1/1997 |
| WO | WO 97/00943 | 1/1997 |
| WO | WO 97/15394 | 5/1997 |
| WO | WO 97/36167 | 10/1997 |
| WO | WO 97/37036 | 10/1997 |
| WO | WO 98/45406 | 10/1998 |
| WO | WO 98/47003 | 10/1998 |
| WO | WO 99/11373 | 3/1999 |
| WO | WO 99/19510 | 4/1999 |
| WO | WO 99/34920 | 7/1999 |
| WO | WO 99/39829 | 8/1999 |
| WO | WO 99/47922 | 9/1999 |
| WO | WO 99/52560 | 10/1999 |
| WO | WO 99/55461 | 11/1999 |
| WO | WO 99/61152 | 12/1999 |
| WO | WO 00/01798 | 1/2000 |
| WO | WO 00/51735 | 9/2000 |
| WO | WO 00/56456 | 9/2000 |
| WO | WO 01/38583 | 5/2001 |
| WO | WO 01/61054 | 8/2001 |
| WO | WO 01/87335 | 11/2001 |
| WO | WO 02/26394 | 4/2002 |
| WO | WO 02/30561 | 4/2002 |
| WO | WO 02/40158 | 5/2002 |
| WO | WO 02/055199 | 7/2002 |
| WO | WO 02/078834 | 10/2002 |
| WO | WO 02/087764 | 11/2002 |

(56) References Cited

FOREIGN PATENT DOCUMENTS

| WO | WO 02/089982 | 11/2002 |
|---|---|---|
| WO | WO 03/002226 | 1/2003 |
| WO | WO 03/035239 | 5/2003 |
| WO | WO 03/042697 | 5/2003 |
| WO | WO 2004/018104 | 3/2004 |
| WO | WO 2004/074818 | 9/2004 |

OTHER PUBLICATIONS

Anonymous, "The Living Chip-Automated Microarray Technology for Homogeneous and Inhomogeneous Bioassays", http://www.nist.gov.public affairs/atp2000/00004362.htm, visited on Jun. 14, 2001, 2 pages.
Arndt et al., "A Rapid Genetic Screening System for Identifying Gene-Specific Suppression Constructs for use in Human Cells", 2000, 28(6), 6, e15-i-viii.
Ausubel et al., "Current Protocols in Molcular Biology", 1987 and annual updates, John Wiley & Sons, pp. iii-xii (Table of Contents).
Birren et al., "Genome Analysis: A Laboratory Manual", Laboratory Press, 1999, v-ix (Table of Contents).
Brenan et al., "A massively parallel microfluidics platform for storage and ultra high throughput screening", 2002, 4626 Proc. SPIE 560-69.
Brown, Charts for Counting Bacterial Colonies, Am. J. Pub. Health Nations Health, 1947, 37, 206-07.
Cheng et al., "Membrane-Tethered Proteins for Basic Research, Imaging and Therapy", Medical Research Reviews, May 14, 2008.
Coleman et al., "Phospholipid Synthesis in Isolated Fat Cells", J. Biological Chem., 1977, 252, 3050-56.
Cooper,"Applications of microarray technology in breast cancer research", Breast Cancer Res., 2001, 3(3) 158-75.
CRC Handbook of Chemistry and Physics, Ed. Robert C. Weast, Ph.D. 65, 1984-1985.
de Macario et al., "Adaptation of the Slide Immuneozymatic Assay for Quantification of DNA Hybridization: SIA-DNA", 8 Biotechniques, 1990, 210-17.
de Macario et al., 121 Methods in Ezymolow, 509-25, 1986.
de Macario et al., Chemical Abstr., 67622t, 1985.
de Macario et al., "Slide Immunoenzymatic Assay for Human IgE(SIAIgE)", J. Immunological Methods, 1986, 90 137-41.
Erfle et al., "Simultaneous loading of 200 sample lanes for DNA sequencing on vertical and horizontal standard and ultrathin gels", Oxford University Pres, 1997, 25(11), 2229-2230.
Gadus, Cadus Pharmaceutical Corp, 1997 Annual Report, May 8, 1998, 1-29.
Gait, "Oligonucleotide Synthesis: A Practical Approach", IRL Press, 1984, vii-xiii (Table of Contents).
Gillmor et al.,"Low-Contact-Angle Polydimethyl Siloxane (PDMS) Membranes for Fabricating Micro-Bioarrays", Proc. 2d Ann. Int'l IEEE-EMBS Spec. Topic Cont. on Microtechnologies in Med. & Bio., 2002, 51.
Huhmer et al., "Noncontact Infrared-Mediated Thermocycling for Effective Polymerase Chain Reaction Amplification of DNA in Nanoliter Volumes", Anal. Chem., 2000 72, 5507-12.
Jones et al., "Dielectrophoretic Liquid Actuation and Nanodroplet Formation", J. Applied Phys., Jan. 15, 2001, 99(2) 1441-42.
Kanigan et al., "Living Chips for drug discovery", 3926 Proc. SPIE, 2000, 172-80.
Kricka et al., Microchip PCR, 377 Anal. Bioanal. Chem., 2003, 820-25.
Lee et al., "A novel real-time PCR machine with a miniature spectrometer for fluorescence sensing in a micro liter value glass capillary", 100 Sensors and Actuators B, 2004, 401-10.
Lennon, "High-throughput gene expression analysis for drug discovery", Drug Discovery Today, Feb. 2000, 5(2), 59-66.
Macbeath et al., "Printing Proteins as Microarrays for high-Throughout Function Determination", Science, Sep. 2000, 289, 1760-1762.
Maniatis, et al., Molecular Cloning: A Laboratory Manual, 1982, Cold Spring Harbor Laboratory Press, v-x (Table of Contents).
Matsubara et al., "Microchamber Array Based DNA Quantification and Specific Sequence Detection from a Single Copy Via PCR in Nanoliter Volumes Biosensors and Bioelectronics", 2005, 20, 1482-1490.
Matsubara et al., "On-chip Nanoliter-Volume Multiplex TaqMan Polymerase Chain Reaction From a Single Copy Based on Counting Fluorescence Released from Microchambers", Anal. Chem., 2004, 21, 6434-6439.
Moerman et al., Miniaturized Electrospraying as a Technic for the Production of Microarrays of Reproducible Micrometer Sized Protein Spots, in Micro Total Analysis Systems 2000, Proceedings of the TAS 2000, May 2000, Symposium, 14-18.
Nagai et al., "Development of a Microchamber Array for Picoliter PCR", Anal. Chem., 2001, 73, 1043-1047.
Nagai et al., "High-Throughput PCR in Silicon Based Mcrochanber Array Biosensors & Bioelectronics", 2001, 16, 1015-1019.
Polakoff et al, "Isolation of Somatic Cell Mutants Defective in the Biosynthesis to Phosphatidylethanolamine", J. BioloQical Chem., 1981, 256, 7687-90.
Prescott et al., Microbiology, 1990 31, 114-116.
Rolls et al., "A Visual Screen of GFP-Fusion Library Identifies a New Type of Nuclear Envelope Membrane Protein", 1999, 146(1), 29-43.
Sambrook, et al., Molecular Cloning: A Laboratory Manual, Cold Spring Harbor laboratory Press, 1989, 2, xi-xxxviii (Table of Contents).
Sauter, Nanoliters onto media: Use of Electric Induction, American Laboratory, Oct. 2001, 40-45.
Shoffner et al., "Chip PCR. I. Surface passivation of microfabricated silicon-glss chips for PC", Nucleic Acids Research, 1996, 24(2) 375-79.
Sieweke, "Direction of Transcription Factor Partners with a Yeast One Hybrid Screen", 2000,130, 59-77.
Singh-Gasson et al., "Maskless fabrication of light-directed oligonucleotide microarrays using a digital micromirror array", Nature Biotechnology, Oct. 1999, 17, 974-978.
Smith et al., "Dynamical Scaling of DNA Diffusion Coefficients", Macromolecules, 1996, 29, 1372-1373.
Sosnowski, "Manufacturing Methods for High Density Micro-Channel Arrays", Masters Thesis, MIT Mechanical Engineering Department, Jun. 2000.
Steel et al., Flow-Thru Chip™: A Three-Dimensional Biochip Platform, in Microarray Biochip Technology, Mark Schena ed. 2000, 87-117.
Taylor et al., "Optimization of the Performance of the Polymerase Chain Reaction in Silicon-Based Microstructures", Nucleic Acids Research, 1997, 25(15), 3164-68.
Thorstenson et al., "Global Analysis of ATM Polymorphism Reveals Significant Functional Constraint", Am. J. Hum. Genet., 2001, 69, 396-412.
Vogelstein et al., "Digital PCR", Pro. Natl. Acad. Sci USA., Aug. 1999, 96, 9236-9241.
Vykoukal et al., "A programmable Dielectrophoretic Fluid Processor for Droplet-Based Chemistry", Micro Total Analysis Systems, 2001, J.M. Ramsey & A. van den Berg eds., 72-74.
Wittwer et al., "Continuous Fluorescence Monitoring of Rapid Cycle DNA Amplification", BioTechniques, Jan. 1997, 22, 130-138.
Wittwer et al., "The Light Cycler: A Microvolume Multisample Fluorimeter with Rapid Temperature Control", BioTechniques, Jan. 1997, 176-181.
Zhao et al., Directed Evolution Converts Subtilisin E into a Functional Equivalent of Thermitase, 1999, 12(1), 47-53.
Zubritsky, "Spotting a microarray system", Modern Drug Discovery, May 2001, 4(5), 59.

SEQUENCE LISTING

<160> NUMBER OF SEQ ID NOS: 10

<210> SEQ ID NO 1

```
<211> LENGTH: 20
<212> TYPE: DNA
<213> ORGANISM: Artificial Sequence
<220> FEATURE:
<223> OTHER INFORMATION: Synthetic forward primer: FrwCAG2

<400> SEQUENCE: 1
ggaccctcgc tgcagcctca                                                     20

<210> SEQ ID NO 2
<211> LENGTH: 28
<212> TYPE: DNA
<213> ORGANISM: Artificial Sequence
<220> FEATURE:
<223> OTHER INFORMATION: Synthetic reverse primer: RewCAG2

<400> SEQUENCE: 2
gcaagtggtc attgagattg agctgcct                                            28

<210> SEQ ID NO 3
<211> LENGTH: 18
<212> TYPE: DNA
<213> ORGANISM: Artificial Sequence
<220> FEATURE:
<223> OTHER INFORMATION: Synthetic forward primer

<400> SEQUENCE: 3
tggtatgacc ggcatcct                                                       18

<210> SEQ ID NO 4
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 4
tcggcgtgtc atatttcact                                                     20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer: Intron 34F

<400> SEQUENCE: 5
caaaagtgtt gtcttcatgc                                                     20

<210> SEQ ID NO 6
<211> LENGTH: 22
<212> TYPE: DNA
<213> ORGANISM: Artificial Sequence
<220> FEATURE:
<223> OTHER INFORMATION: Synthetic primer: Intron 34R

<400> SEQUENCE: 6
ctgcaacaaa ttgacaacta gt                                                  22

<210> SEQ ID NO 7
<211> LENGTH: 25
<212> TYPE: DNA
<213> ORGANISM: Artificial Sequence
<220> FEATURE:
<223> OTHER INFORMATION: Synthetic primer: Intron 48F

<400> SEQUENCE: 7
```

```
taagatagtc cctgacaagt agtta                                              25

<210> SEQ ID NO 8
<211> LENGTH: 24
<212> TYPE: DNA
<213> ORGANISM: Artificial Sequence
<220> FEATURE:
<223> OTHER INFORMATION: Synthetic primer: Intron 48R

<400> SEQUENCE: 8
tgacatatgg gaataaatac tttt                                               24

<210> SEQ ID NO 9
<211> LENGTH: 29
<212> TYPE: DNA
<213> ORGANISM: Artificial Sequence
<220> FEATURE:
<223> OTHER INFORMATION: Synthetic probe: Intron 34
<220> FEATURE:
<221> NAME/KEY: misc_feature
<223> OTHER INFORMATION: Labelled with FAM and TAMRA

<400> SEQUENCE: 9
tttaaaaaat tacttctaga taatccgca                                          29

<210> SEQ ID NO 10
<211> LENGTH: 29
<212> TYPE: DNA
<213> ORGANISM: Artificial Sequence
<220> FEATURE:
<223> OTHER INFORMATION: Synthetic probe: Intron 48
<220> FEATURE:
<221> NAME/KEY: misc_feature
<223> OTHER INFORMATION: Labelled with TET and TAMRA

<400> SEQUENCE: 10
ttgctgcttt cattattatt attattcat                                          29
```

APPARATUS AND METHODS FOR PARALLEL PROCESSING OF MICRO-VOLUME LIQUID REACTIONS

CROSS REFERENCE TO RELATED APPLICATIONS

This application is a continuation of U.S. patent application Ser. No. 12/582,652 filed Oct. 20, 2009 and issued as U.S. Pat. No. 8,053,185, which is a divisional under 35 U.S.C. §120 of U.S. patent application Ser. No. 11/054,184, filed Feb. 9, 2005, and issued as U.S. Pat. No. 7,604,983 on Oct. 20, 2009, which is a continuation of U.S. patent application Ser. No. 09/935,455, filed Aug. 22, 2001, now abandoned, which is a continuation-in-part of U.S. patent application Ser. No. 09/789,899, filed Feb. 20, 2001, now abandoned, which claims the benefit of U.S. Provisional Application Ser. No. 60/229,357, filed Feb. 18, 2000. Each of which is hereby incorporated by reference in its entirety.

TECHNICAL FIELD

This invention is related to devices and processes for carrying out multiple simultaneous micro-reactions in liquid samples.

BACKGROUND

Reactions that are conducted in solution such as, for example, chemical, biological, biochemical and molecular biological reactions, are frequently carried out within a chamber or other container. Such chambers, or reaction vessels, are commonly made of glass or plastic and include, for example, test tubes, microcentrifuge tubes, capillary tubes and microtiter plates. Reaction chambers currently in use are not amenable for use with volumes below one microliter, due to problems such as large head volumes in the reaction chamber leading to evaporative losses of the reaction solution, and difficulty in adding and removing reaction mixtures from the reaction chamber.

Many types of biochemical reactions, for example, nucleic acid amplification, require temperature cycling. Many reaction chamber materials are poor thermal conductors, thus there are time lags associated with changing the temperature of the reaction vessel and equilibration of a temperature change throughout the sample volume. Such lags in temperature change and temperature equilibration lead to longer cycle times, non-uniform reaction conditions within a single reaction, and lack of reproducibility among multiple reactions, both simultaneous and sequential.

It is often necessary to carry out a series of experiments on a set of identical samples. Usually this set of samples must be serially duplicated, either manually or by means of robotic liquid delivery systems. These processes can be slow, as they depend on the total number of samples to be duplicated and, if applicable, the speed of the robot.

Efforts to address the aforementioned problems have included the use of robotics and the use of capillary thermal cyclers, e.g., the Light Cycler® (Idaho Technologies). See Wittwer et al. (1997a) BioTechniques 22:130-138, and Wittwer et al. (1997b) BioTechniques 22:176-181. However, such methods and apparatuses still require sample volumes of several microliters, involve difficult liquid handling procedures such as loading and emptying capillaries, and can involve detection problems associated with capillary geometry and spacing.

Microarrays comprising an ordered array of biological molecules (e.g., peptides, oligonucleotides) on a solid surface are known. See, for example, U.S. Pat. Nos. 5,445,934; 5,510,270; 5,605,662; 5,632,957; 5,744,101; 5,807,522; 5,929,208 and PCT publication WO 99/19510. While these are useful for analyzing multiple molecules under identical, conditions (e.g., hybridizing a plurality of different oligonucleotide sequences with a single probe or probe mixture), such a "chip" cannot be used for analysis of multiple samples under multiple experimental conditions. Furthermore, such arrays are limited to analysis of molecules which can either be synthesized on the array substrate or covalently attached to the substrate in an ordered array. In addition, molecules tethered to an array react with slower kinetics than do molecules in solution, and are sterically hindered in their interactions resulting in altered reaction kinetics. Additionally, for arrays of proteins and peptides, surface interactions affect the natural conformation of proteins under investigation (MacBeath and Schreiber, Science, vol 289, pp. 1760-1763).

WO 99/34920 discloses a system and method for analyzing a plurality of liquid samples, the system comprising a platen having two substantially parallel planar surfaces and a plurality of through-holes dimensioned so as to maintain a liquid sample in each through-hole by means of surface tension. WO 00/56456 discloses a method for holding samples for analysis and an apparatus thereof includes a testing plate with a pair of opposing surfaces and a plurality of holes. WO 99/47922 discloses vascularized perfused microtissue/micro-organ arrays. U.S. Pat. No. 5,290,705 discloses a specimen support for optical observation or analysis, the support comprising a disc-like member composed of a rigid material and having at least one unobstructed hole extending therethrough.

Polynucleotides may be sheared through transfer methods such as pipetting. One method for reducing polynucleotide shear is to use pipet tips with the tip ends cut off for polynucleotide transfer. Other methods for reducing polynucleotide shear have been described in U.S. Pat. Nos. 6,147,198; 4,861,448; 5,599,664; 5,888,723; and 5,840,862.

There is a continued need for apparatuses and methods suitable for microvolume liquid reactions. There is also a need for improved methods of transferring polynucleotides.

All references cited herein are hereby incorporated by reference in their entirety.

SUMMARY

Disclosed herein are apparatuses for containing multiple micro-volume samples and conducting multiple simultaneous micro-volume chemical and biochemical reactions in an array format, methods utilizing the apparatuses, and kits containing the apparatuses.

The embodiments of the invention include, but are not limited to, the following.

An apparatus for containing multiple micro-volume liquid samples comprising a substrate, wherein the substrate defines a plurality of sample chambers, wherein each sample chamber: (a) extends through the substrate, (b) comprises one or more walls and an opening at each end, and (c) holds a sample such that the sample is in the form of a thin film such that a liquid sample present in one sample chamber does not intermix with a liquid sample present in another sample chamber; and wherein the sample chamber has a height to width ratio of less than 1:1, wherein the height of the sample chamber is measured from one face of the substrate to the other. The apparatus may comprise at least one component of a reaction to be carried out in the apparatus. In one embodiment the component is a reagent used in a nucleotide sequencing reaction. In another embodiment the component is one used in a hybridization reaction. In another embodiment, the apparatus is substantially free from contaminating amplifiable polynucleotides.

In another aspect of the invention, an apparatus for containing multiple micro-volume liquid samples comprising a substrate is provided, wherein the substrate defines a plurality of sample chambers, wherein each sample chamber: (a) extends through the substrate, (b) comprises one or more walls and an opening at each end, and (c) holds a sample such that the sample is retained in the apparatus through surface tension and such that a liquid sample present in one sample chamber does not intermix with a liquid sample present in another sample chamber; wherein the apparatus is substantially free of contaminating amplifiable polynucleotides; and wherein the apparatus comprises at least one reagent used in a polynucleotide amplification reaction to be carried out in the apparatus. In one embodiment, the apparatus comprises at least two reagents used in a polynucleotide amplification reaction to be carried out in the apparatus. In a preferred embodiment, the sample chamber has a height to width ratio of about 1:1, wherein the height of the sample chamber is measured from one face of the substrate to the other. The polynucleotide amplification reaction may be, for example, a polymerase chain reaction, a ligase chain reaction, or a rolling circle amplification reaction.

For apparatuses disclosed herein, the reaction component(s) may optionally be affixed to the solid substrate. In some embodiments the reaction component is affixed to the solid substrate by drying.

In a preferred embodiment, the substrate comprises hydrophobic regions; the hydrophobic regions are located on the substrate such that a liquid sample present in one sample chamber does not intermix with a liquid sample present in another sample chamber.

In an embodiment of the apparatus, the hydrophobic regions are located on the upper and lower faces of the substrate such that the openings of at least one sample chamber from at least one adjacent sample chamber by a hydrophobic region. The hydrophobic regions may also be located on the walls of the sample chambers. In some embodiments the hydrophobic region forms an annular ring along the wall of the sample chamber. In some embodiments the apparatus comprises two or more hydrophobic regions, each forming an annular ring along the wall of the sample chamber, and the hydrophobic regions define one or more annular non-hydrophobics rings therebetween.

In another embodiment of the apparatus the substrate can comprise an upper face and a lower face. A further refinement of this embodiment is wherein the through axes of the sample chambers are perpendicular to both faces of the substrate. The sample chamber may also have the shape of, for example, a right circular cylinder or a right polygonal prism.

Other embodiments of the invention are methods that are carried out in a microhole apparatus. These methods include the following:

A method for simultaneously conducting a plurality of micro-volume reactions, the method comprising: (a) introducing a plurality of liquid samples into the sample chambers of a microhole apparatus, wherein the samples contain necessary reaction components; and (b) placing the apparatus into an environment favorable to the reaction; wherein the microhole apparatus comprises a substrate, wherein the substrate defines a plurality of sample chambers, wherein each sample chamber: (i) extends through the substrate; (ii) comprises one or more walls and an opening at each end; and holds a sample such that the sample is in the form of a thin film such that a liquid sample present in one sample chamber does not intermix with a liquid sample present in another sample chamber; and wherein the sample chamber has a height to width ratio of less than 1:1, wherein the height of the sample chamber is measured from one face of the substrate to the other.

The environment can be one to prevent evaporation, such as a hydrophobic medium or a humidified chamber. In some embodiments the apparatus is substantially free of contaminating amplifiable polynucleotides. In some embodiments the reactions can be ligation reactions, primer extension reactions, nucleotide sequencing reactions, restriction endonuclease digestions, oligonucleotide synthesis reactions, hybridization reactions, and biological interactions. The biological interactions can be avidin-biotin interactions, streptavidin-biotin interactions, antigen-antibody interactions, hapten-antibody interactions and ligand-receptor interactions. In some embodiments the reaction component is affixed to the substrate. In some embodiments the results of the reactions are monitored. Monitoring can be by a number of methods, including optical monitoring, mass spectrometry and electrophoresis. Monitoring can be of the progress of the reactions during the course of the reactions. In some of the methods of the invention one or more of the reactions are supplemented with one or more reagents during the course of the reaction.

In another method of the invention utilizing a microhole apparatus is one for adding a component to a microvolume reaction. The method comprises the steps of: A method for adding a component to a micro-volume reaction, wherein the method comprises the steps of: (a) providing a first apparatus comprising a first sample chamber containing a reaction mixture; (b) providing a second apparatus comprising a second sample chamber containing the component; and (c) bringing the apparatuses into proximity such that liquid contact is established between the first sample chamber and the second sample chamber; wherein each apparatus comprises a substrate, wherein the substrate defines a plurality of sample chambers, wherein each sample chamber: (i) extends through the substrate; (ii) comprises one or more walls and an opening at each end; and (iii) holds a sample such that the sample is in the form of a thin film such that a liquid sample present in one sample chamber does not intermix with a liquid sample present in another sample chamber; and wherein the sample chamber has a height to width ratio of less than 1:1, wherein the height of the sample chamber is measured from one face of the substrate to the other. In another embodiment of the method multiple components are added to a reaction, by providing additional apparatuses, wherein each of the components is present in a sample chamber of an apparatus. Another embodiment comprises simultaneously adding a component to a plurality of micro volume reactions wherein, in the method described above, the apparatuses are brought into proximity such that liquid contact is established between corresponding sample chambers of the apparatuses. In a preferred embodiment the component is a nucleic acid.

A method for adding a nucleic acid to a micro-volume reaction is provided, wherein the method comprises the steps of: (a) providing a first apparatus comprising a first sample chamber containing a reaction mixture; (b) providing a second apparatus comprising a second sample chamber containing the nucleic acid; and (c) bringing the apparatuses into proximity such that liquid contact is established between the first sample chamber and the second sample chamber; wherein each apparatus comprises a substrate, wherein the substrate defines a plurality of sample chambers, wherein each sample chamber: (i) extends through the substrate; (ii) comprises one or more walls and an opening at each end; and (iii) holds a sample such that the sample is retained in the apparatus through surface tension and such that a liquid sample present in one sample chamber does not intermix with a liquid sample present in another sample chamber.

A method for introducing a liquid sample into a sample chamber is provided, wherein the method comprises the steps of: (a) contacting an apparatus with a liquid solution; and (b) removing the apparatus from the solution; wherein the apparatus comprises a substrate, wherein the substrate defines a plurality of sample chambers, wherein each sample chamber: (i) extends through the substrate; (ii) comprises one or more walls and an opening at each end; and (iii) holds a sample such that the sample is in the form of a thin film such that a liquid sample present in one sample chamber does not intermix with a liquid sample present in another sample chamber; and wherein the sample chamber has a height to width ratio of less than 1:1, wherein the height of the sample chamber is measured from one face of the substrate to the other.

In another embodiment of the invention, a method for introducing a liquid sample comprising a nucleic acid into a sample chamber is provided, wherein the method comprises the steps of: (a) contacting an apparatus with a liquid solution comprising a nucleic acid; and (b) removing the apparatus from the solution; wherein the apparatus comprises a substrate, wherein the substrate defines a plurality of sample chambers, wherein each sample chamber: (i) extends through the substrate; (ii) comprises one or more walls and an opening at each end; and (iii) holds a sample such that the sample is retained in the apparatus through surface tension and such that a liquid sample present in one sample chamber does not intermix with a liquid sample present in another sample chamber.

In another embodiment of the invention, a method for diluting a solution is provided, wherein the method comprises the steps of: (a) providing a first apparatus comprising a first sample chamber containing the solution (b) providing a second apparatus comprising a second sample chamber containing a diluent; and (c) bringing the apparatuses into proximity such that liquid contact is established between the first sample chamber and the second sample chamber; wherein each of the apparatuses comprises a substrate, wherein the substrate defines a plurality of sample chambers, wherein each sample chamber: (i) extends through the substrate; (ii) comprises one or more walls and an opening at each end; and (iii) holds a sample such that the sample is in the form of a thin film such that a liquid sample present in one sample chamber does not intermix with a liquid sample present in another sample chamber; and wherein the sample chamber has a height to width ratio of less than 1:1, wherein the height of the sample chamber is measured from one face of the substrate to the other.

In another embodiment of the invention, a method for diluting a solution comprising a nucleic acid is provided, wherein the method comprises the steps of: (a) providing a first apparatus comprising a first sample chamber containing the solution which comprises a nucleic acid; (b) providing a second apparatus comprising a second sample chamber containing a diluent; and (c) bringing the apparatuses into proximity such that liquid contact is established between the first sample chamber and the second sample chamber; wherein each of the apparatuses comprises a substrate, wherein the substrate defines a plurality of sample chambers, wherein each sample chamber: (i) extends through the substrate; (ii) comprises one or more walls and an opening at each end; and (iii) holds a sample such that the sample is retained in the apparatus through surface tension and such that a liquid sample present in one sample chamber does not intermix with a liquid sample present in another sample chamber.

In preferred embodiments for the methods described above a plurality of solutions may be simultaneously diluted wherein the apparatuses are brought into proximity such that liquid contact is established between corresponding sample chambers of the apparatuses. In another preferred embodiment, steps (b) through (c) are repeated one or more times using a new second apparatus containing fresh solvent at each repetition of step (b).

In another embodiment of the invention, a method for selective retention of a molecule in a first sample chamber is provided, wherein the method comprises the steps of: (a) providing a first apparatus, wherein the first sample chamber contains a solution comprising the molecule and one or more additional solute molecules of higher diffusibility; providing a second apparatus comprising a second sample chamber containing a solvent; bringing the apparatuses into proximity such that liquid contact is established between the first sample chamber and the second sample chamber; and (d) removing the apparatuses from proximity; wherein each of the apparatuses comprises a substrate, wherein the substrate defines a plurality of sample chambers, wherein each sample chamber: (i) extends through the substrate; (ii) comprises one or more walls and an opening at each end; and (iii) holds a sample such that the sample is in the form of a thin film such that a liquid sample present in one sample chamber does not intermix with a liquid sample present in another sample chamber; and wherein the sample chamber has a height to width ratio of less than 1:1, wherein the height of the sample chamber is measured from one face of the substrate to the other.

A method for selective retention of a nucleic acid in a first sample chamber is provided, wherein the method comprises the steps of: (a) providing a first apparatus, wherein the first sample chamber contains a solution comprising the nucleic acid and one or more additional solute molecules of higher diffusibility; (b) providing a second apparatus comprising a second sample chamber containing a solvent; (c) bringing the apparatuses into proximity such that liquid contact is established between the first sample chamber and the second sample chamber; and (d) removing the apparatuses from proximity; wherein each of the apparatuses comprises a substrate, wherein the substrate defines a plurality of sample chambers, wherein each sample chamber: (i) extends through the substrate; (ii) comprises one or more walls and an opening at each end; and (iii) holds a sample such that the sample is retained in the apparatus through surface tension and such that a liquid sample present in one sample chamber does not intermix with a liquid sample present in another sample chamber.

In a preferred embodiment of these methods, the method is used for desalting a solution. In another preferred embodiment, steps (b) through (d) are repeated one or more times using a new second apparatus containing fresh solvent at each repetition of step (b). In another preferred embodiment, a plurality of solutions may be simultaneously desalted, wherein the apparatuses are brought into proximity such that liquid contact is established between corresponding sample chambers of the apparatuses.

A method for parallel electrophoretic analysis of a plurality of micro-volume reactions is provided, wherein the method comprises: (a) conducting the reactions in a microhole apparatus; (b) placing the apparatus in contact with an electrophoresis medium; and (c) conducting electrophoresis; wherein the apparatus comprises a substrate, wherein the substrate defines a plurality of sample chambers, wherein each sample chamber: (i) extends through the substrate; (ii)

comprises one or more walls and an opening at each end; and (iii) holds a sample such that the sample is retained in the apparatus through surface tension and such that a liquid sample present in one sample chamber does not intermix with a liquid sample present in another sample chamber. The apparatus can be placed with one face in contact with the electrophoresis medium. In another embodiment the electrophoresis medium is contained within the sample chambers of one or more additional apparatuses. In other embodiments, in the additional apparatuses the corresponding sample chambers are aligned.

Another method for use in the invention comprises a method for preparing a plurality of samples for mass spectrometric analysis, wherein the samples are placed in an apparatus that comprises a substrate, wherein the substrate defines a plurality of sample chambers, wherein each sample chamber: (a) extends through the substrate; (b) comprises one or more walls and an opening at each end; and (c) holds a sample such that the sample is retained in the apparatus through surface tension and such that a liquid sample present in one sample chamber does not intermix with a liquid sample present in another sample chamber. The analysis can be conducted by matrix assisted laser desorption ionization time-of-flight (MALDI-TOF) spectrometry. These methods can be used to detect a genetic polymorphism, for example, a single nucleotide polymorphism (SNP). Detection may consist of, for example, mass differences due to a single base primer extension.

A method for mixing a plurality of micro-volume samples is provided, the method comprising: (a) providing a first microhole apparatus comprising a substrate, wherein the substrate defines a plurality of sample chambers, wherein each sample chamber: (i) extends through the substrate; (ii) comprises one or more walls and an opening at each end; and (iii) holds a sample such that the sample is retained in the apparatus through surface tension and such that a liquid sample present in one sample chamber does not intermix with a liquid sample present in another sample chamber; (b) providing a second microhole apparatus comprising a substrate, wherein the substrate defines a plurality of sample chambers, wherein each sample chamber: (i) extends through the substrate; (ii) comprises one or more walls and an opening at each end; and (iii) holds a sample such that the sample is retained in the apparatus through surface tension and such that a liquid sample present in one sample chamber does not intermix with a liquid sample present in another sample chamber; and (c) bringing the apparatuses into proximity such that liquid contact is established between more than one sample chamber from the first apparatus and a sample chamber in the second apparatus. In one embodiment, the holes in the first apparatus may be smaller than the holes in the second, allowing more than one hole from the first apparatus to simultaneously contact a single hole in the second apparatus.

A method for simultaneously conducting a plurality of micro-volume polynucleotide amplification reactions is provided, the method comprising: (a) introducing a plurality of liquid samples into the sample chambers of a microhole apparatus, wherein the samples contain necessary polynucleotide amplification reaction components; and (b) placing the apparatus into an environment favorable to the polynucleotide amplification reaction; wherein the microhole apparatus comprises a substrate, wherein the substrate defines a plurality of sample chambers, wherein each sample chamber: (i) extends through the substrate; (ii) comprises one or more walls and an opening at each end; and (iii) holds a sample such that the sample is retained in the apparatus through surface tension and such that a liquid sample present in one sample chamber does not intermix with a liquid sample present in another sample chamber; and wherein the apparatus is substantially free of contaminating amplifiable polynucleotides. In one embodiment, the environment is selected from the group consisting of a hydrophobic medium and a humidified chamber. In another embodiment, the polynucleotide amplification reaction is a polymerase chain reaction. In other embodiments, the polynucleotide amplification reaction is a ligase chain reaction or a rolling circle amplification reaction. In some embodiments, the results of the reactions are monitored. The results may be monitored by, for example, optical monitoring, mass spectrometry and electrophoresis. In another embodiment, the progress of the reactions is monitored during the course of the reactions. In yet another embodiment, one or more of the reactions are supplemented with one or more reagents during the course of the reaction. In a preferred embodiment, a reagent is affixed to the substrate. In another preferred embodiment, the analysis is used to detect a genetic polymorphism. In yet another preferred embodiment, the analysis is used to analyze gene expression levels.

Still other embodiments of the invention are kits containing the microhole apparatuses described Supra, for the methods of the invention. These include the following.

A kit comprising an apparatus for containing multiple micro-volume liquid samples comprising a substrate, wherein the substrate defines a plurality of sample chambers, wherein each sample chamber: (a) extends through the substrate, (b) comprises one or more walls and an opening at each end, and (c) holds a sample such that the sample is in the form of a thin film such that a liquid sample present in one sample chamber does not intermix with a liquid sample present in another sample chamber; and wherein the sample chamber has a height to width ratio of less than 1:1, wherein the height of the sample chamber is measured from one face of the substrate to the other, and further comprising a reaction component packaged in a suitable container. The reaction component may be a reagent for performing a reaction selected from the group consisting of, for example, ligation reactions, primer extension reactions, nucleotide sequencing reactions, restriction endonuclease digestions, oligonucleotide synthesis, hybridization reactions and biological interactions.

A kit comprising an apparatus for containing multiple micro-volume liquid samples comprising a substrate is provided, wherein the substrate defines a plurality of sample chambers, wherein each sample chamber: (a) extends through the substrate, (b) comprises one or more walls and an opening at each end, and (c) holds a sample such that the sample is retained in the apparatus through surface tension and such that a liquid sample present in one sample chamber does not intermix with a liquid sample present in another sample chamber; wherein the apparatus is substantially free of contaminating amplifiable polynucleotides, and further comprising a polynucleotide amplification reaction component packaged in a suitable container.

In one embodiment of the above described kits, the reaction component may be affixed to the substrate. In another embodiment, the kit may further comprise a hydrophobic substance to be used with the apparatus. The hydrophobic substance can be, for example, a hydrophobic fluid packaged in a suitable container and/or a hydrophobic cover. The kit may also further comprise a chamber for maintaining the appropriate environmental conditions for a reaction to be carried out in the apparatus. The kit may also further comprise an apparatus for loading the samples into the sample chambers.

As will be apparent to one of skill in the art, any method or technique which requires parallel processing, display and/or storage of multiple micro-volume samples will be facilitated by the use of the apparatuses disclosed herein.

DETAILED DESCRIPTION OF ILLUSTRATIVE EMBODIMENTS

Modes for Carrying Out the Invention

Figure 1:
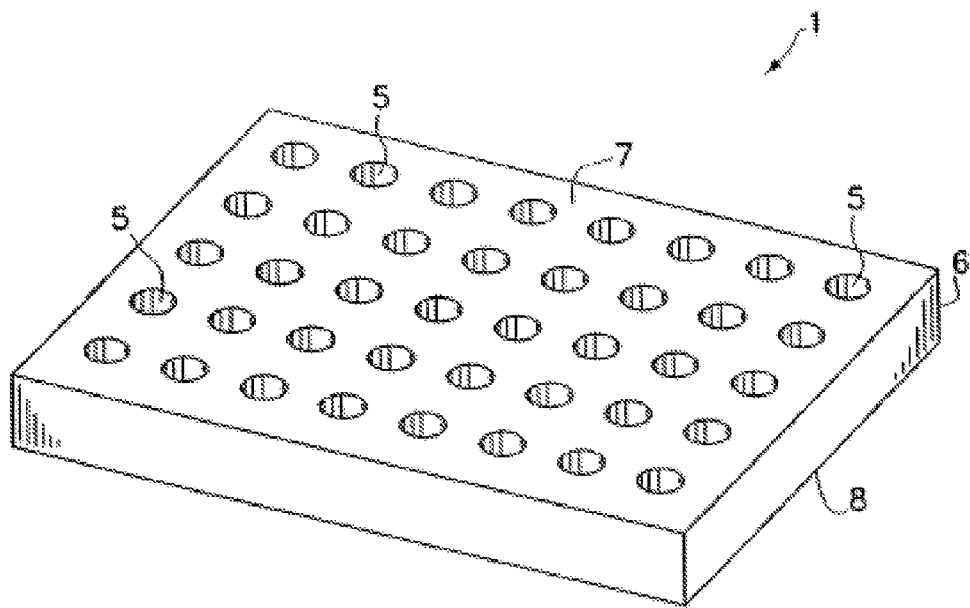
FIG. 1 is a perspective view of one embodiment of the claimed apparatus, in the form of a microhole array.

General Methods:

The practice of the invention employs, unless otherwise indicated, conventional techniques in photolithography, chemical etching, general machining, microfluidics, organic chemistry, biochemistry, oligonucleotide synthesis and modification, nucleic acid hybridization, molecular biology, microbiology, genetic analysis, recombinant DNA, and related fields as are within the skill of the art. These techniques are described in the references cited herein and are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987 and annual updates); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991); Birren et al. (eds.) GENOME ANALYSIS: A LABORATORY MANUAL, Cold Spring Harbor Laboratory Press, 1999.

The disclosures of all publications and patents cited herein are hereby incorporated by reference in their entirety.

Definitions

The terms "plate" and "substrate" denote the solid portion of an apparatus.

A characteristic of a "thin-film" sample, as disclosed herein, is that a sample is contained in a sample hole and remains therein through the action of surface tension and/or adhesion to the inner wall of the hole. Preferably, a thin film is a liquid sample in which the diffusion time is no more than about four-fold greater, more preferably no more than about three-fold greater, more preferably no more than about two-fold greater, more preferably no more than about one-fold greater in one dimension that in any other dimension. Preferably, the temperature conductance characteristics of a thin film sample are no more than about four-fold greater, more preferably no more than about three-fold greater, more preferably no more than about two-fold greater, even more preferably no more than about one-fold greater in one dimension that in any other dimension. Most preferably, a thin film will have hydrodynamic and thermal properties equivalent to a solution contained in a right circular cylinder having a depth: diameter ratio of about 4:1, or more preferably about 3:1 or less, about 2:1 or less, more preferably about 1:1, even more preferably less than 1:1. Methods for measuring hydrodynamic properties, diffusion time and thermal conductance characteristics are well-known to those of skill in the art.

Two or more holes in an apparatus are denoted "corresponding holes" if they occupy the same relative position on two or more different apparatuses such that, if the apparatuses are aligned face-to-face, the holes communicate with one another.

"Polynucleotide", "oligonucleotide", and "nucleic acid", are used interchangeably herein to refer to polymers of nucleotides of any length, and include natural, synthetic, and modified nucleic acids.

"Substantially free of contaminating amplifiable polynucleotides", as used herein, is meant to indicate an apparatus which is substantially free from contaminating polynucleotides, such as DNA or RNA, which may interfere with the analysis. Such an apparatus is suitable for use in performing assays such as, for example, amplification reactions, e.g. PCR reactions, in which contaminating amplifiable polynucleotides may coamplify along with the desired amplification product(s), thus interfering with the analysis.

Apparatuses

Disclosed herein are apparatuses and methods for simultaneous parallel processing, display and/or storage of a plurality of micro-volume liquid samples, wherein an apparatus comprises a substrate containing a plurality of micro-sample chambers. In one embodiment, the sample chambers are micro-through-holes, such that the apparatus comprises an array of micro-through-holes in a substrate. The apparatus can have any shape consonant with the purposes for which it is used. In one embodiment, the apparatus is rectangular; however, triangular, circular and ovoid shapes, among others, are also useful. An array of microholes, as disclosed herein, can be used, for example, as a micro-volume sample holder and/or to conduct multiple parallel reactions.

Microholes can be placed in any arrangement within a substrate that is suitable for the experimental purpose of the apparatus. In one embodiment, holes are arranged in rows and columns on a rectangular substrate. The size and/or shape of an apparatus can vary, and is designed with the particular experimental use of the apparatus in mind. For example, if the apparatus is to be used for gel loading or if the products of a reaction conducted in the apparatus are to be analyzed by gel electrophoresis (see infra), the size and shape of the apparatus can be designed to match that of a gel electrophoresis apparatus or sample comb.

Figure 2:
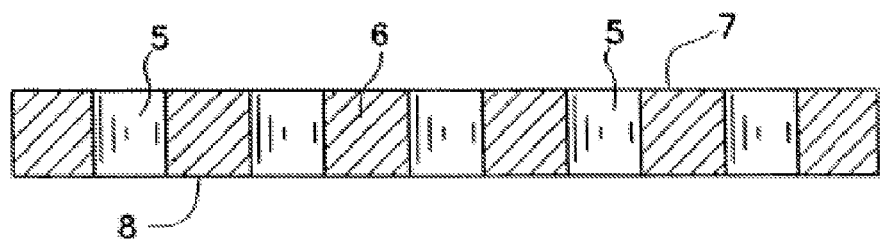
FIG. 2 is a side view (cutaway) through one row of an exemplary apparatus.

An exemplary embodiment of the apparatus is described with reference to FIGS. 1 and 2, wherein the apparatus 1 comprises an array of micro-through-holes contained in a substrate 6, such as a plate, wafer, film or slide, such substrate in one embodiment being substantially thin and planar, and having an upper surface 7 and a lower surface 8. In one embodiment, one or more of the surfaces of the substrate are rendered hydrophobic so that liquid reaction mixtures contained in the micro-through-holes will, by force of surface tension and adhesion, remain fixed therein. In another embodiment, the substrate is flexible. In yet another embodiment, the substrate is a curved plane. An exemplary use of the latter embodiments is to bend the substrate into a cylinder and place a rotating optical scanner inside the cylinder to monitor the reactions in the microholes.

Figure 3A:
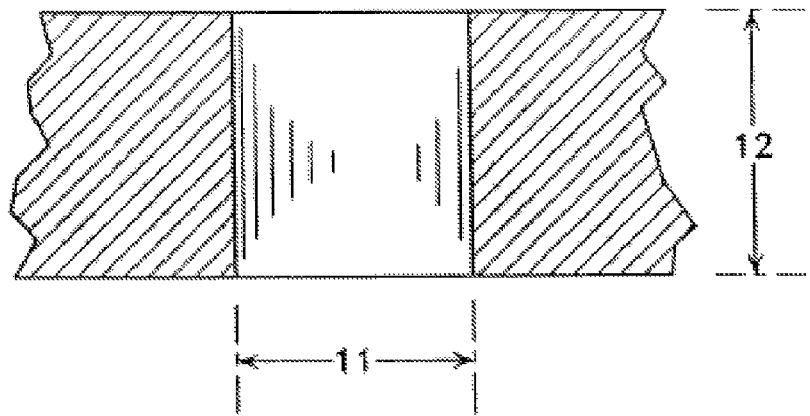
FIGS. 3A and 3B show side (cutaway) views of a single exemplary sample chamber.
Figure 3B:
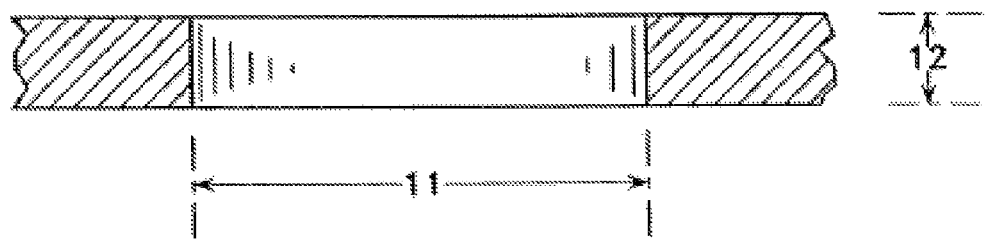

Any size and/or shape of the sample chamber, that is consistent with the retention of liquid therein through surface tension and is commensurate with the use of the apparatus, can be chosen. In one preferred embodiment, the sample chambers are in the shape of a right polygonal prism, for example, a right rectangular prism. Although, in a preferred embodiment, the sample chambers are in the shape of right circular cylinders with parallel walls, it is clear that the walls of a sample chamber could be convex (i.e., bowed inward) or concave (i.e., bulged outward). Additional sample chamber configurations will be apparent to those of skill in the art and, indeed, any shape of sample chamber consistent with the retention of liquid therein through surface tension is useful. In one embodiment, the height of the hole is greater than about four times the width. In other embodiments, the height of the hole is less than or equal to about four times the width, less than or equal to about three times the width, less than or equal to about 2.5 times the width, less than or equal to about two times the width, equal to about one times the width, less than one times the width, less than or equal to about 0.5 times the width. In another preferred embodiment, the height is equal to or less than the width. In a preferred embodiment, the height of the hole is about 1 times the width. In this embodiment, the sample chamber is a microhole having an aspect ratio with a width 11 roughly equal to depth 12. See FIG. 3A for the case of a cylindrical sample chamber. In additional embodiments, the width 11 is greater than the depth 12. See FIG. 3B, again directed to the exemplary case in which the sample chamber is a cylinder. Thus, in a preferred embodiment, the diffusion time across the height is equal to or less than the diffusion time across the width. For a hole having the shape of a right circular cylinder, the height:width ratio can also be expressed as the ratio of depth to diameter.

The size of the holes is commensurate with the reaction volume and can be varied by varying the width (or diameter) of the hole and/or the thickness of the substrate (which effectively varies the height or depth of the hole). Thus, the volume of a reaction which can be contained in a hole is a function of the height of the hole and the width of the hole. However, a hole can be loaded such that the liquid extends beyond the physical boundaries of the hole; in some cases this will be facilitated if the surface of the substrate surrounding the openings of the holes comprises a hydrophobic material; in other cases, it will be accomplished by surface tension. In this fashion, a volume of liquid which is greater than the volume of the hole can be accommodated by a sample chamber. Conversely, a hole can be loaded with a volume of liquid that is less than the volume of the hole, such that the liquid sample forms a biconcave film. Thus the shape of the sample can range from a biconvex disc through a flat disc to a biconcave disc. Accordingly, sample volumes of less than about 10000 nl, preferably less than about 1000 nl, preferably less than about 500 nl, preferably less than about 100 nl, more preferably less than about 250 nl, more preferably less than about 100 nl, more preferably, less than about 50 nl can be reliably achieved. In one embodiment, sample volumes as low as 5 nl are used. Thus, sample volumes contemplated range from about 1 nl to about 10000 nl.

Each sample chamber can contain an individual sample, or a sample chamber can contain multiple samples separated by hydrophobic regions along the wall of the sample chamber. Thus, in one embodiment, the entire inner wall of a sample chamber is hydrophilic and the sample chamber contains a single sample. In another embodiment, the inner wall of a sample chamber is hydrophobic. In another embodiment, hydrophobic regions are located on the walls of the sample chambers. In a further embodiment, a hydrophobic region forms an annular ring along the wall of the sample chamber. Such a hydrophobic ring can be used, for example, to divide a sample chamber into two regions. Dual-region sample chambers can be used, for example, to temporarily isolate different reaction components prior to mixing by, for example, physical agitation, insertion and optionally movement of a probe and/or heating (e.g., interior laser heating). Such a configuration is useful in the practice of methods such as, for example, hot-start PCR. Additional applications of such a configuration will be apparent to those of skill in the art.

Figure 4A:
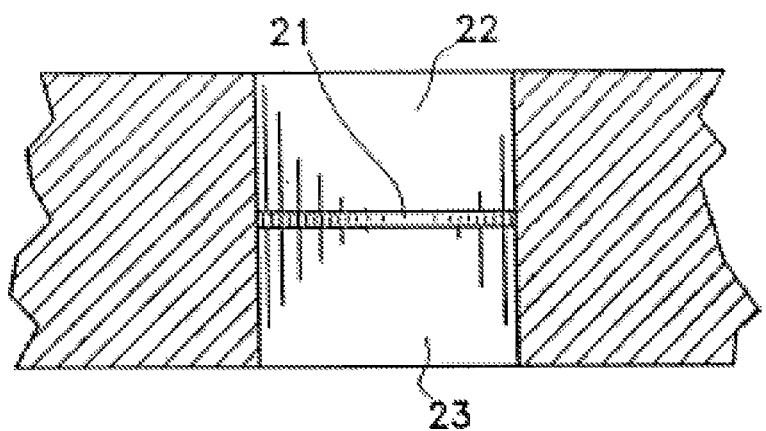
FIGS. 4A and 4B show side (cutaway) views of exemplary sample chambers containing alternating hydrophobic and hydrophilic regions.
Figure 4B:
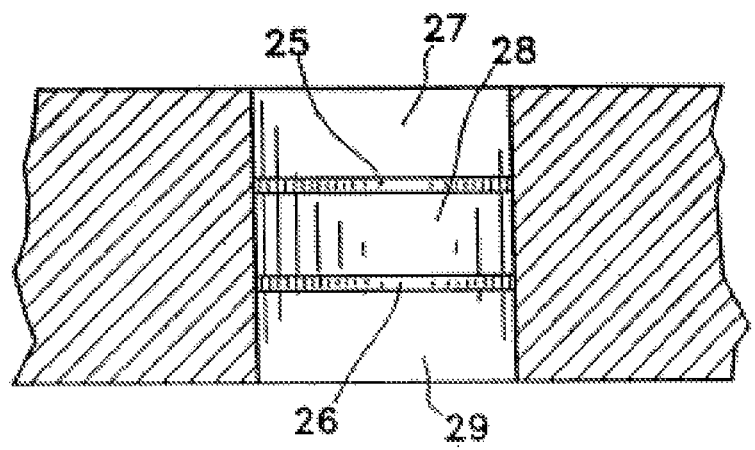

In accord with this embodiment, FIG. 4A shows a schematic diagram of an example of a microhole sample chamber containing annular hydrophobic region 21 along its wall, separating hydrophilic regions 22 and 23. In additional embodiments, the wall of a sample chamber comprises two or more hydrophobic regions, each forming an annular ring along the wall of the sample chamber, thereby defining a plurality of annular non-hydrophobic rings. One example is diagrammed in FIG. 4B, which shows a schematic diagram of an exemplary microhole sample chamber containing annular hydrophobic regions 25 and 26 along its wall, interspersed with annular hydrophilic regions 27, 28 and 29.

Hydrophobic and/or hydrophilic regions along the wall of a sample chamber need not form a continuous 360° ring, nor need they be in the shape of an annulus or portion thereof. Arcs or spots of hydrophilic and/or hydrophobic regions can be present, as required by the particular use of the apparatus. For example, a hydrophobic annular ring, separating two aqueous samples, can be interrupted by a small hydrophilic arc, the presence of which facilitates eventual mixing of the samples. In another example, a small hydrophilic region can be present on the wall of the sample chamber such that an aqueous sample can be concentrated and optionally dehydrated onto the small hydrophilic region. This can facilitate mass spectrometric analysis of a sample, by concentrating the sample into a small target for the laser that is used to launch the sample for mass spectrometry.

Apparatuses comprising holes with hydrophilic and hydrophobic regions located on the walls of the sample chamber may be constructed, for example, by laminating plates comprising different materials together with, for example, epoxy. For example, a titanium plate with chemically etched holes can be laminated on both sides to plastic plates also etched with corresponding holes, yielding an apparatus with microholes having an annular hydrophilic ring surrounded by annular rings of hydrophobic regions.

In one embodiment, the apparatus is a plate with holes passing through in a direction perpendicular to at least one face of the plate. In another embodiment, the faces are parallel to each other, and the radial axis (i.e., the through axis) of each hole is parallel to the walls of the chamber and perpendicular to the faces of the plate. In a more preferred embodiment, the holes have the shape of right circular cylinders. See, for example, FIG. 1. In another preferred embodiment, they have the shape of a right polygonal prism. The holes can be arranged in any configuration that is suitable to an experiment, e.g., an array of one or more rows and one or more columns, the array being a square array of holes, a triangular array of holes or another configuration of holes. The surface of the plate can be prepared or treated so that it repels water or other aqueous solutions, thus ensuring that small volumes of sample which are deposited in the holes will remain in the holes without the possibility of leakage or cross contact with samples in other holes.

The spacing between the holes can be varied to accommodate the density and pattern of holes on the substrate, so long as mixing between adjacent sample chambers does not occur. The substrate can have from about 1 to about 10,000 microholes per apparatus. In preferred embodiments there are at least about 600 microholes per apparatus, more preferably at least about 800 microholes per apparatus, and even more preferably at least about 1000 microholes per apparatus.

Evaporation may be minimized by providing an evaporation covering sheet on the planar surfaces of the substrate which covers the through-holes and retains vapors within the reaction chamber. Such a sheet may be comprised of any material which does not interfere with the reaction contained in the chamber. Such a sheet may be hydrophobic in nature and may by flexible, such as silicone rubber, or may be substantially rigid such as a polymeric or glass cover slide, and may comprise an adhesive substance. The cover is preferably optically clear.

The top and bottom surfaces of the substrate may contain raised features which form closed curves circumscribing the openings to some or all of the sample chambers contained therein. Such features can be used in conjunction with an evaporation retention sheet to improve the reliability of said sheet to prevent loss of vapor. Preferably such raised features are very narrow such that under a moderate force a very high pressure is maintained at the interface of said feature(s) and the adjacent evaporation sheet. Additionally, a single raised feature may circumscribe more than one reaction chamber and thus allow communication between all reaction chambers contained therein.

In a preferred embodiment, the apparatus is substantially free of amplifiable contaminating polynucleotides, particularly for reactions in which contaminating amplifiable polynucleotides may interfere with the reaction, e.g. PCR. Preferably, the apparatus has less than 1000 amplifiable contaminating polynucleotides per reaction chamber, more preferably less than 10 amplifiable contaminating polynucleotides per reaction-chamber, even more preferably less than 1 amplifiable contaminating polynucleotides per reaction chamber. Contaminating amplifiable polynucleotides may be eliminated from the apparatus by, for example, .gamma.-irradiation. The presence of contaminating amplifiable polynucleotides may be detected by, for example by performing a control PCR reaction with no polynucleotide sample; a control reaction which yields polynucleotides indicates the presence of contaminating amplifiable polynucleotides.

Substrates

Numerous materials and methods are available for designing an apparatus for multiple micro-volume liquid samples. Materials that can be used for the substrate include, but are not limited to, titanium sheet preferably treated to render the surface hydrophobic, glass plates with chemically etched holes and silanated surfaces, plastics, teflon, synthetics, metals and ceramics. Techniques of electrodeposition manufacturing, and printed-circuit board manufacturing processes can also be used in the fabrication of the apparatus. In one embodiment, the substrate has a hydrophobic surface and each sample chamber has hydrophilic interior walls. In another embodiment the hydrophilic region of the interior of at least one of the sample chambers extends to the surface of the substrate and extends beyond the orifice defined by the sample chamber such that the area occupied by the extended portion is substantially contained on the substrate surface and such that the hydrophilic region of one sample chamber does not contact the hydrophilic region of any other sample chamber. Such a hydrophilic region may aid in loading aqueous reactions into the reaction chamber.

Titanium is bio-inert, hydrophilic, and can be chemically etched to provide a dense array of holes in any pattern desired. It is also very durable and hence reusable. Photo-etched titanium substrates are also useful for fabrication and are available, for example, from Tech-Etch, Plymouth, Mass.

Glass plates rendered hydrophobic by a surface treatment, for example, by silanation are also suitable; since glass is hydrophilic and silanation renders its surface hydrophobic. Silicon microfabrication is a suitable method for fabrication of apparatuses comprising extremely well defined, high density arrays of sample chambers.

Advances in the field of printed-circuit (PC) board manufacturing can be applied to the fabrication of the apparatus. Current printed circuit board technology provides both miniaturization and cost efficiency.

An additional process which can be used in the fabrication of an apparatus as disclosed herein is photolithographic electrodeposition. This technique involves slowly depositing metal ions (electroplating) onto a substrate in a photolithographically defined pattern. This technology reliably produces through-holes of 1 µm diameter, and can produce over 3 million holes per square inch. In one embodiment, this technology is used for fabrication of an apparatus comprising very high density microhole arrays. Photolithographically fabricated substrates are available, for example, from Metrigraphics, Wilmington, Mass.

Other techniques for fabrication known in the art may be used for constructing the apparatuses of the invention, for example, laser micromachining and microfabrication techniques.

Sample Delivery and Recovery

Delivery of samples and reagents to a microhole can be achieved manually, or through the use of commercially available pipetting robots, such as those available from the Hamilton Company, Reno, Nev. and the Packard Instrument Co., Meriden, Conn. Currently-available pipetting robots can reliably deposit sample volumes as small as 50 nl, and a robotic positional repeatability of 50 µm is common. Higher accuracy and repeatability can be achieved through special design, such as by the coupling of piezoelectric and mechanical translation devices (e.g., Physik Instrumente, Costa Mesa, Calif. For dispensing reagent volumes in the sub-nanoliter range, piezo-electric pipettors and ink-jet pipettors, for example, can be used.

Thus, reactions can be prepared in the microholes of the apparatus by any means commonly used for dispensing small liquid volumes into small vessels including, but not limited to: (1) dispensing very small volumes of reagent directly into each hole, either manually or by means of a robotically controlled syringe, (2) immersing the entire apparatus, or a predetermined fraction thereof, directly into a reaction solution, thereby acquiring a volume of reaction solution in each hole that has been immersed, and (3) dispensing, pouring over or flowing over the surface of the substrate a volume of the reaction mixture. In another embodiment, reaction components are affixed within a sample chamber, for example, by placing a solution within the sample chamber and drying it, such that a solute is affixed to the wall of a sample chamber. Reaction mixtures and/or additional reagents are then added to the chamber, re-solubilizing the affixed reaction component. In preferred embodiments, more than one, more than two, more than three reagents may be affixed to the wall of a sample chamber. For PCR reactions, for example, primers, probes, and/or buffer components can be preaffixed to the sample chambers, allowing for faster preparation times.

After initial addition of reagent, subsequent reagent additions can be conducted. Means for adding additional reagent to a microhole include, but are not limited to, the previously-described methods, as well as: (1) direct dispensing, either manually or by means of, for example, a robotically controlled syringe, (2) direct dispensing into the reaction solution by a non-contact means such as a piezo-electric dispensing apparatus, (3) deposition of a vaporized solution of reagent, and (4) contact between two or more of the apparatuses, such that material in a hole from one apparatus is transferred wholly or in part to a hole in another apparatus. In one embodiment, transfer occurs between corresponding holes in two or more apparatuses.

Figure 5A:
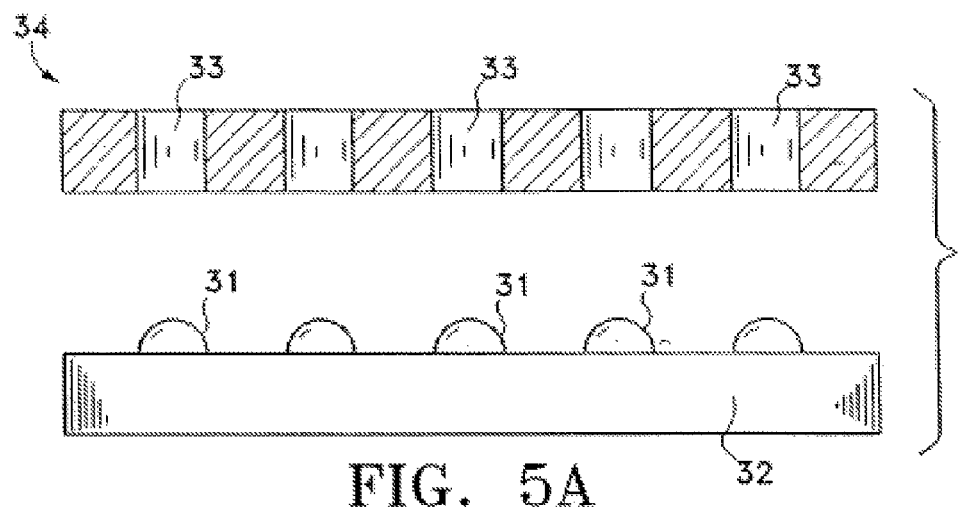
FIGS. 5A, 5B and 5C show simultaneous loading of multiple individual samples into discrete sample chambers by contacting an exemplary apparatus with an arrangement of liquid samples on a hydrophobic surface.
Figure 5B:
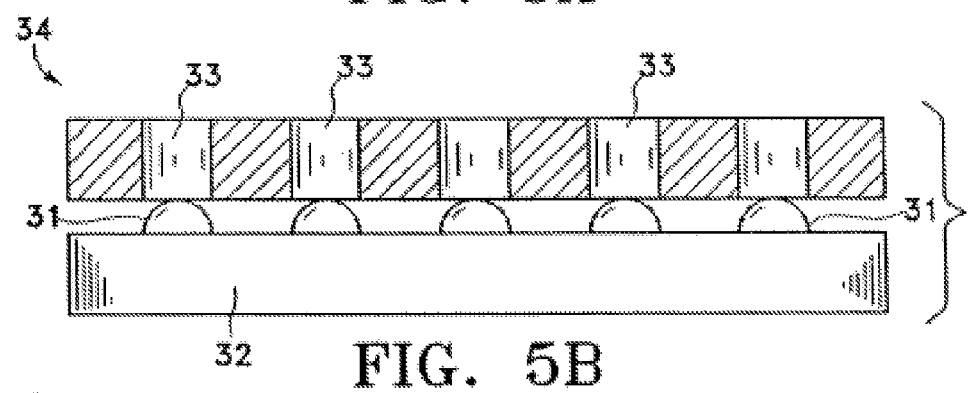
Figure 5C:
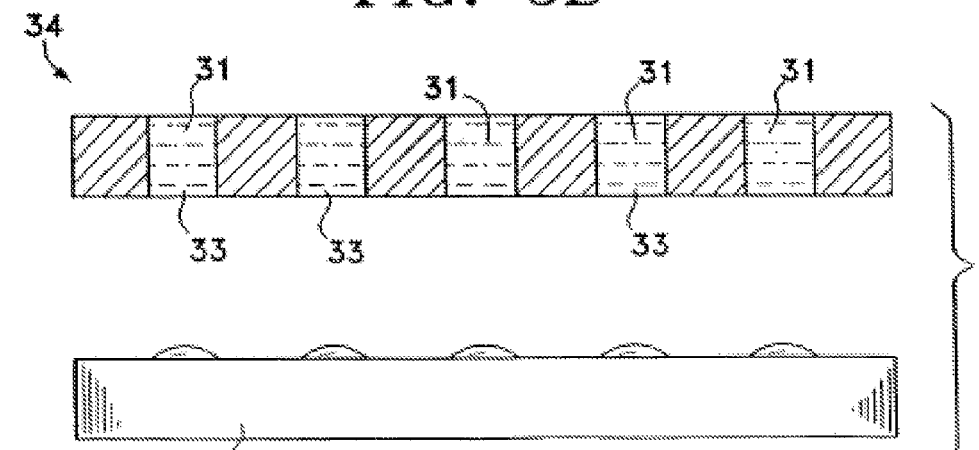

An additional exemplary method for sample delivery to sample chambers in an apparatus is shown schematically in FIG. 5. In this embodiment, samples 31 are arranged on a hydrophobic surface 32 in a pattern that matches the pattern of holes 33 in an apparatus 34. FIG. 5A. The apparatus 34 is then brought into proximity with the hydrophobic surface 32, such that the samples 31 contact the holes 33 in the apparatus 34. FIG. 5B. The apparatus is then withdrawn from proximity with the surface, the holes 33 now containing samples 31 (FIG. 5C).

The process of liquid transfer from one apparatus to another can also be used to make several copies of a single setup plate simultaneously. For example, if a group of microhole array plates are stacked, one on top of another, and liquid samples are introduced into the top or bottom plate, the samples will wick through the entire stack, thereby generating a series of plates having identical sample configurations.

Furthermore, contents of a sample chamber, or of an entire apparatus, can undergo dilution, particle size selection, selective retention of a molecule in a sample chamber, desalting, reagent addition, or another chemical modification by bringing the apparatus, or a portion thereof, in liquid contact with one or more additional apparatuses, the additional apparatus(es) prepared in such a way that contact between apparatuses will, by chemical diffusion from one sample chamber on one apparatus to the another sample chamber on an adjacent apparatus, achieve the required sample modification. See infra.

After reaction assembly in an apparatus is complete, the apparatus can subsequently undergo chemical processing and/or incubation in a thermally-controlled environment. A concern when dealing with minute aqueous samples, such as are present in the sample chambers of the apparatus, is evaporation. One way in which this problem can be mitigated is by conducting incubation in a high-humidity environment. For example, various types of water vaporizers are readily available and can be easily integrated into a laboratory device to provide a humidified chamber. Other methods of reducing evaporation include, but are not limited to, placing the apparatus in a humidified chamber, maintaining the atmosphere of an open apparatus at saturated vapor pressure, and periodic addition of water to the reactions by means of a piezo-electric or other dispenser in a manner which counteracts the evaporation rate.

Alternatively, the apparatus can be immersed in a hydrophobic medium such as, for example, a bath of an inert liquid that is essentially non-miscible with water and which essentially does not react with the substrate nor essentially perturb the reaction(s) contained in the sample chamber(s). In many applications an example of a suitable hydrophobic medium is oil, for example, mineral oil or silicone oil.

Reactions contained in the sample chambers of an apparatus can be thermally cycled in such a way as to carry out, for example, amplification reactions such as a polymerase chain reaction (PCR) or DNA sequencing reactions such as, for example, chain-termination sequencing and cycle sequencing. In such thermal cycling reactions, evaporation of the sample can be minimized by submerging the sample in a hydrophobic medium such as, for example, a bath of hydrophobic medium or other suitable fluid which is maintained at a temperature appropriate for the chemical reaction, by coating the apparatus with a layer of hydrophobic fluid, or by overlaying the samples with a hydrophobic fluid. For example, addition of samples to sample chambers can be followed by direct addition of a film of oil or other hydrophobic fluid to each sample using a pair of robotic pipets; one filled with a sample and the other filled with the hydrophobic fluid.

If, for example, an oil bath is used for temperature control, temperature cycling can be achieved by thermally cycling the bath, or by robotically moving an apparatus from one bath to another bath held at a different temperature. Alternatively, thermal cycling of reactions contained in an array of microholes can be carried out in a humidified environment, maintained by sealing the array between one or two evaporation barriers (e.g., silicone sheets or Parafilm®), and placing this sandwiched array on a thermoelectric heating block, or between two thermoelectric heating blocks. In using an evaporation barrier such as a silicone sheet, the presence of narrow raised features circumscribing each sample chamber or a set of sample chambers to aid in preventing the loss of vapor by providing a very tight seal around each hole.

Means for dispensing water to counter evaporation can also be used to dispense other reagents or chemicals of interest, mixed in a solution such that evaporation is countered. In this way, chemical assays can be carried out in real time and the evolution of the assay can be directed via feedback from the assay in progress. To provide but one example, optical data obtained by placing the apparatus on an optical detector, such as a CCD or fiber optics cable, can be input to a computer which automatically adjusts reagent dispensers and guides them to dispense a precise amount of reagent into each sample chamber.

Advantages

The apparatuses disclosed herein, when used, for example, in a biochemical reaction format, provide the advantages of: (1) high density, (2) high throughput, (3) ease of handling, (4) performance of very low-volume reactions (5) rapid thermal cycling, and (6) advantageous optical access of the samples. In embodiments in which the apparatus is moved from one thermal environment to another, the thin-film nature of the samples ensures very rapid thermal equilibration time. In an alternative embodiment in which an apparatus is held stationary in a thermoelectric (Peltier) device and the temperature of the device is changed, apparatuses having a planar symmetry allow two thermoelectric devices to be used, one on each side of the apparatus. This provides a sample ramp speed at least twice that obtained when a single Peltier device is used, as well as finer control of the temperature profile within the sample.

Further benefits of the microhole array format of the apparatus include the ability to transfer liquids from one sample chamber in a first apparatus to another sample chamber in a second apparatus simply by bringing two apparatuses in close enough proximity to allow the contents of two sample chambers to touch. Upon physical contact the two samples will diffuse together. This technique allows sample mixing, sample dilution and diffusion-based molecular separations e.g., de-salting. The contents of a sample chamber in a first apparatus can be transferred, in whole or in part, to a sample chamber in a second apparatus.

For sample mixing, two apparatuses are brought into contact, as above, such that the liquid contents of one or more pairs of sample chambers come into liquid contact, wherein one member of each pair of sample chambers is present in a first apparatus and the other member is present in a second apparatus. Mixing of three or more samples, using three, four, etc. apparatuses is also possible, as will be evident to one of skill in the art. This is particularly advantageous when being used to transfer nucleic acids, such as DNA and RNA, from one apparatus to another. Nucleic acids are easily sheared by methods such as pipeting, and this method allows for the transfer of nucleic acids without the need for pipetting.

For sample dilution, a first apparatus containing one or more samples is contacted with a second apparatus containing diluent, such that liquid contact is achieved between one or more sample chambers in the first apparatus and one or more sample chambers in the second apparatus, and the apparatuses are allowed to remain in contact for a specified time. In this case, all components in the sample are diluted, with the degree of dilution depending on the time of contact between the first and second apparatuses. If all samples in a first apparatus are to be diluted, the first apparatus need not be contacted with a second apparatus, but can simply be contacted with a pool of diluent.

Selective retention of a molecule in a sample chamber, dependent on diffusion-based separation of low molecular weight molecules from molecules of high molecular weight, is possible using the apparatuses as disclosed herein. For example, a sample contained in a microhole is desalted by repeatedly touching the sample, for a short time, to a bath (or to a microhole of another apparatus) containing a solution of very low salt concentration. Since very small molecules (such as salts) diffuse very rapidly (approximately 60 µm per second), while larger molecules take much longer to diffuse (e.g., a 2 kilobase nucleic acid has a diffusion rate of approximately 6 µm per second, see, for example, Smith et al. (1996) Macromolecules 29:1372-1373), an overall reduction in salt concentration of the sample is achieved.

In one embodiment, two apparatuses having identical patterns of sample chambers are contacted so as to bring corresponding sample chambers into contact. Two (or more) sample chambers are "corresponding" if they are located in the same position on different apparatuses (i.e. if each apparatus comprises an array of microholes, corresponding microholes occupy the same location in the array). In additional embodiments for selective, diffusion-based molecular retention, desalting, dilution and/or reagent addition, contact between corresponding sample chambers is not required. For example, a single sample-chamber in a first apparatus can be contacted with multiple, different sample chambers of a second apparatus. In a separate embodiment, subsets of chambers in a first apparatus are contacted with sets of chambers in a plurality of additional apparatuses.

Another advantage of the apparatus format of the invention is the ability to minimize shear when loading a microhole array with a nucleic acid. Nucleic acids, such as DNA and RNA, are easily sheared by transfer methods such as pipetting. The apparatus of the invention may be loaded with a solution comprising a nucleic acid simply by contacting the apparatus with a liquid solution, for example, contacting the apparatus with a tray containing the solution of interest (e.g., "dip loading").

In some embodiments, formation of a thin film by a sample, when it is contained in a sample chamber of the apparatus, results in a ratio of surface area to volume that facilitates optical analysis of the sample, either continuously during the reaction period or at one or several predetermined time points. Because photons pass through a minimum fluid volume in the thin film, more efficient detection of light absorption and emission (e.g., fluorescent, chemiluminescent) by a sample is possible. Furthermore, because of these favorable optical properties, progress of multiple reactions can be monitored in real time (i.e., during the course of the reaction). For example, in reactions that generate an optical signal, e.g. a colored, fluorescent, or luminescent product, reaction progress can be monitored in real time for instance using multiple optical detectors aligned with the sample chambers, fiber optics, a detector that scans across the apparatus, or a whole-apparatus imager. Compared to analysis of micro-volume reactions in capillaries, the apparatuses disclosed herein allow improved optical analysis that is not prone to either refractive effects from capillary walls or optical cross-talk between neighboring capillaries.

Applications

Apparatuses as disclosed herein can be used for holding and arraying any type of liquid micro-volume sample. They can also be used for performing any type of biochemical or molecular biological reaction known to one of skill in the art including, but not limited to, nucleotide sequencing (e.g., chain-termination sequencing, cycle sequencing), amplification reactions (e.g., polymerase chain reactions), transcription, reverse transcription, restriction enzyme digestion, ligation, primer extension, other enzymatic reactions and biological interactions (such as, for example, avidin-biotin, streptavidin-biotin, antibody-antigen and ligand-receptor interactions). In general, any type of enzyme-mediated reaction can be performed in the apparatus. In addition, multiple micro-volume hybridization reactions can be conducted in the apparatus. In one embodiment, an apparatus is used for very high throughput analysis of chemical samples; for example, in combinatorial chemistry. Several exemplary applications are disclosed below, including those in the Examples, and additional applications are known to those of skill in the art. Use of the apparatuses disclosed herein will be especially useful in the field of genetic analysis, for techniques such as polymorphism detection (see infra).

Amplification Reactions

Very high throughput of small volume amplification reactions, such as polymerase chain reactions, ligase chain reactions, rolling circle amplification, and "Taqman®" hydrolyzable probe assays is obtained using, for example, an apparatus containing an array of microholes. The ability to perform a large number of individual reactions, each in a very small volume, obviates the need for multiplex PCR (in which several different genomic loci are amplified in a single reaction) and avoids the technical difficulties inherent in that strategy. Alternatively, low-number multiplex reactions can be carried out in a microhole format, compounding the benefits of this technology.

In many applications of PCR, recovery of an amplification product is desirable. Problems with recovery of amplification products using methods of the prior art are related to the elevated temperatures used for most amplification reactions, necessitating the use of an oil overlay to prevent evaporation of the reaction mixture. In these cases, the presence of oil can interfere with recovery of the amplification product(s), for example, making it difficult to aspirate a microvolume sample. Methods which do not require the use of oil (e.g., conducting amplification reactions in capillaries) still present problems with fluid manipulation.

This problem can be addressed by use of apparatuses as disclosed herein. For example, a porous hydrophobic membrane that is preferably essentially non-reactive (such as a teflon membrane filter) can be used in conjunction with an apparatus. In this embodiment, an apparatus containing a plurality of reactions is immersed in an oil bath for conducting a high-temperature reaction, removed from the bath, and touched to the porous hydrophobic membrane. The hydrophobic medium will readily wet the hydrophobic membrane and flow into it, whereas an aqueous reaction solution will be repelled. Subsequent removal of the apparatus from the hydrophobic membrane leads to the formation of discrete drops of aqueous solution resting thereon. These aqueous drops can be readily accessed. Alternatively, direct pipetting of an aqueous reaction solution from beneath a hydrophobic substance layer on hydrophobic surface is possible with accurate and reliable robotics.

Moreover, for certain applications, the presence of a hydrophobic substance is not a hindrance. For example, when an apparatus is used for loading reaction products into an acrylamide gel (see infra), the apparatus (optionally having been used as a reaction sheet) can be placed onto the top of a gel and overlayed with upper reservoir buffer. After addition of buffer, the hydrophobic substance separates from the buffer layer, thereby separating from the gel samples.

Molecular Haplotyping

Knowing the haplotype, or the "phase" of the genotypes of an individual is far more informative than simply knowing the genotypes alone. Standard methods of haplotyping involve a statistical analysis of the genotype distributions, often relying on assumptions regarding the recombination rate of the genetic region and the size of the recombined region. The apparatus and methods described herein may be advantageously used to experimentally identify the haplotype.

Following the digital-PCR application outlined by Vogelstein and Kinzler (PNAS, vol. 96, p. 9236-9241), the microhole apparatuses described herein may be used to provide high confidence haplotype information by performing hundreds or thousands of PCR reactions simultaneously on a DNA template.

The technique requires individual amplifications of single molecules of DNA. Such single molecule amplification can only be achieved on the average by applying a terminally diluted sample of template DNA to an array of microholes. On average half of the holes will contain exactly zero copies of the DNA region of interest, somewhat less than half will have exactly one copy, and fewer still will have two or more copies. The distribution of number of holes with a given number of templates should follow a Poisson statistical distribution. DNA samples may be prepared, for example, by using the Stratagene DNA Extraction kit (Stratagene, La Jolla, Calif.) according to manufacturer's instructions, and then diluted to a concentration of one-half genome equivalent per reaction.

The tests may be performed, for example, by using fluorescent dual labelled probes and the 5-prime exonuclease (TaqMan) assay. In this assay a probe is added to the PCR brew which is designed to hybridize to a sequence of interest within the PCR amplicon. The probe is synthesized with two fluorescent molecules—an emitter and a quencher. These two molecules are each attached to individual bases on the probe and are spaced typically 5-7 bases apart so that the quencher molecule prohibits the emitter from fluorescing. As a single unit the dual-labelled probe is non-fluorescing. During the PCR process a probe molecule will hybridize to the template molecule which is being polymerized, and as the Taq polymerase synthesizes the complement to the template, the 5-prime to 3-prime exonuclease activity of the Taq polymerase will degrade and displace the hybridized primer. This degradation separates the emitter from the quencher molecule and thus allows the emitter molecule to fluoresce. This emission can be read by a standard fluorescent plate reader and the intensity of the fluorescence is generally quantitatively related to the number of initial template molecules. Probe molecules which do not stringently hybridize are not degraded and will not fluoresce.

Thus, the final distribution of the sequence(s) of interest may be obtained by counting the number of single fluorescent unit intensity microholes versus zero intensity microholes (where a unit of intensity is derived by comparing the brightness of each hole; the holes which started out with two templates should have approximately twice the brightness of most of the remaining fluorescent microholes, which should have started with only a single template molecule).

An apparatus (or "chip") of the invention may be loaded with the appropriate PCR reactants, for example, by dip-loading a solution containing the PCR reactants, or by pipetting (preferably with a large bore pipet) the solution(s) into the microholes. The apparatus may be preloaded with one or more reactants. The apparatus is preferably sealed with, for example, a single sheet of clear adhesive film (such as parcel packaging tape) folded around one edge and sealed at the opposite edge with a face-to-face adhesive seal.

The apparatus is thermal cycled in a thermal cycler which may be modified by milling or sawing a narrow, deep groove across its face so that the thin microhole chip may be inserted into the groove and the chip reliably thermal cycled. Preferably, a thin heat-conductive silicone pad (Stockwell Rubber Company, Philadelphia, Pa.) is used to provide thermal contact as well as pressure to the surfaces of the microhole chip. The added pressure prevents evaporation of the samples.

Following thermal cycling, the chip is scanned using a scanner or fluorescent microscope to determine the levels of fluorescence, in order to determine the final distribution of the sequence(s) of interest.

Very-High Throughput PCR

High throughput PCR is readily achieved using, for example, microhole arrays by dispensing template, reagent, and primer pairs to each microhole. Typically, two of these steps are combined: for instance the template and reagent (enzyme, buffer, etc.) are combined in a master mix and the master mix is loaded simultaneously into all microholes by dipping an apparatus into a solution of master mix or by spraying a solution of master mix over an apparatus such that the solution enters the sample chambers. A significant increase in throughput is achieved by pre-affixing oligonucleotide primers and probes to each chamber, or by pre-synthesis of all primer pairs in a microhole array. In this case, reactions can then be assembled simply by immersing a pre-synthesized microhole array plate into a bath of master mix.

Technologies for pre-synthesis of primers on the apparatus include: standard phosphoramidite and photo-phosphoramidite chemistries. Standard phosphoramidite chemistry is used for most oligonucleotide synthesis operations when it is necessary to recover the oligonucleotide in solution for later use. See, for example, U.S. Pat. Nos. 4,415,732; 4,458,066; 4,500,707; 4,973,679; and 5,153,319. Photo-phosphoramidite chemistry, for synthesizing oligonucleotides on a solid substrate for later use on that substrate, has been disclosed, for example, in U.S. Pat. Nos. 5,445,934; 5,510,270; and 5,744,101; and PCT publication WO 99/19510. Using photo-phosphoramidite chemistry, substrates containing up to 10,000 discrete oligonucleotides can be obtained. In one embodiment, an output array is controlled by an array of micro-mirrors and optical elements and is highly flexible. Singh-Gasson et al. (1999) Nature Biotechnology 17:974-978.

Thus, this technique is suitable for forming arrays for use in highly parallel processing and can be adapted for synthesizing oligonucleotides in, for example, an array of microholes.

Cycle Sequencing

Figure 6A:
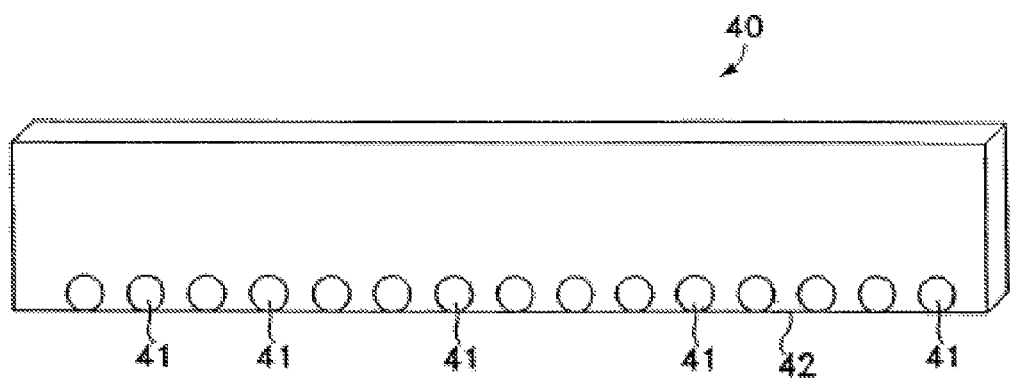
FIGS. 6A, 6B and 6C are top views of exemplary apparatuses that can be used for gel loading.
Figure 6B:
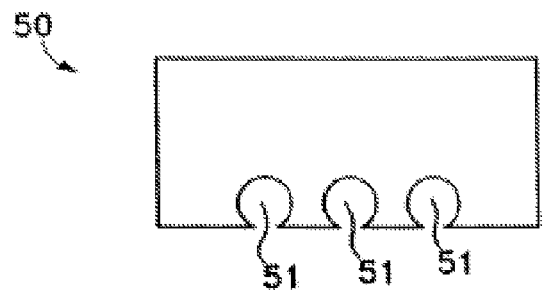
Figure 6C:
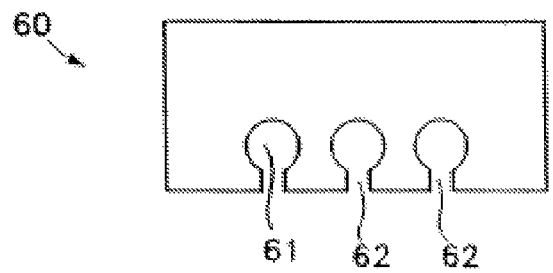

Small volume cycle sequencing reactions can be performed in a high throughput setting, in a fashion similar to the PCR application, supra. An additional benefit of the technology disclosed herein is the ability to perform sequencing reactions directly on the comb or plate that will be used for loading the reaction product onto the sequencing apparatus. For instance, for using standard slab gel electrophoresis sequencing apparatus, reactions are performed in a 1-dimensional array of holes which has been pre-formed on a gel loading comb. See, for example, Erfle et al. (1997)—Nucleic Acids Res. 25(11'):2229-2230. Sequencing reactions are assembled in the array of holes on the comb and, after completion of thermal cycling; the reaction product is directly loaded onto a gel for electrophoresis. FIG. 6 depicts several embodiments of this type of array. FIG. 6A shows an apparatus 40 in which the sample chambers 41 are located close to one edge 42 of the apparatus. FIG. 6B shows a portion of an apparatus 50 in which the sample chambers 51 communicate with the exterior of the apparatus. FIG. 6C shows a portion of an apparatus 60 in which the sample chambers 61 communicate with the exterior of the apparatus via channels 62. Additional configurations of the apparatus suitable for gel loading will be apparent to those of skill in the art.

Endonuclease Reactions

Standard room temperature or elevated temperature restriction endonuclease digestions can be performed using the disclosed apparatuses. An endonuclease reagent mastermix is loaded into each sample chamber, either by automated pipetting means or by immersing, for example, a microhole array into a bath of reagent. Subsequently, individual samples of, for example, nucleic acid and/or restriction endonuclease, can be loaded into each well using an automated pipettor or other means. After the reactions are assembled the apparatus is incubated at a temperature appropriate for the assay. If the duration and temperature of the incubation is such that evaporation of the samples may be a problem, the incubation can take place in a humidified chamber or under a hydrophobic substance to counter or mitigate the effects of evaporation. See supra.

Biological Interactions

The strong biochemical interaction between biotin and streptavidin (or avidin) has made these molecules useful for binding assays. For example, incorporation of a biotin-labeled nucleotide into a polynucleotide, and subsequent capture of the polynucleotide with streptavidin, is a common method for isolating a specific polynucleotide sequence. A biotin-streptavidin capture is easily performed using the disclosed apparatus by simply touching an apparatus, optionally containing biotin-labeled samples, to a plate or substrate which has streptavidin bound to its surface. The plate can be a membrane, microscope slide, cover slip, or another microhole array with streptavidin bound to the inner wall of the sample chambers.

Other pairs of interacting molecules can also be used in a similar fashion. Examples include, but are not limited to, antigen-antibody, hapten-antibody, sugar-lectin, and ligand-receptor.

Oligonucleotide Synthesis

In another embodiment for performing chemical reactions, an apparatus such as a microhole array is used as a miniature oligonucleotide synthesizer, utilizing standard phosphoramidite chemistry and electrical addressing. It is a straightforward extension of microfabrication technologies as used in integrated circuit production to design a microhole array in which each hole can be individually charged or uncharged. See, for example, U.S. Pat. Nos. 5,605,662; 5,632,957; and 5,929,208 for related techniques used in the construction of a microarray. Using such techniques, a different oligonucleotide can be synthesized at each hole in a multi-step process. At each step, the array is exposed to a nucleotide monomer, and the sites on the array containing oligomers to which that monomer is to be added are electrically addressed so as to direct the monomer to those sites.

Such a device would have the multiple advantages of producing oligonucleotides in a predetermined location as well as producing smaller amounts of oligonucleotide required for a particular reaction, leading to increased economy and efficiency.

Genetic Analysis

An important result of the efforts to determine human (and other) genome sequences is the availability of a vast pool of genetic data (in the form of DNA sequence) which can be subjected to a multitude of genetic analyses. The results of the various genetic analyses can be applied to diagnostic, pharmacogenomic and therapeutic applications, to name but a few. One particularly valuable form of genetic information—that is available through the analysis of DNA sequence is genetic polymorphism. Polymorphism can be due to insertion, deletion, translocation, transposition and/or tandem repetition of particular portions of a sequence, or to single- or multiple-nucleotide changes at particular positions within a sequence.

Many methods known in the art can be used to determine the presence of a genetic polymorphism. For example, insertions and deletions, as well as some types of transposition and translocation, can be detected by restriction fragment length polymorphisms (RFLPs).

Another method for determining the presence of a polymorphism is by analysis of tandem repeat lengths in minisatellite DNA. This technique involves restriction enzyme digestion and blot hybridization, and/or STRP analysis, which involves PCR, gel electrophoresis or primer extension and mass spectrometry. See, for example, Birren et al. (eds.) "Genome Analysis: A Laboratory Manual" Cold Spring Harbor Laboratory Press, 1999, esp. Volume 4 Polymorphisms resulting from a single nucleotide change ("SNP") may or may not result in a change in the size of a restriction fragment. A multitude of additional techniques, known to those of skill in the art, are available for the detection of SNPs. These include, but are not limited to, denaturing gradient gel electrophoresis, single-strand conformation polymorphism analysis, heteroduplex analysis, temperature gradient gel electrophoresis, cleavase-fragment length polymorphism, denaturing HPLC, chemical cleavage of mismatch, carbodiimide modification, enzymatic cleavage of mismatch, uracil-N-glycosylase-mediated T scan, direct nucleotide sequencing, DNA chip resequencing, allele-specific primer extension, oligonucleotide ligation assay, randomly amplified polymorphic DNA analysis ("RAPD"), fluorescence energy transfer dye terminator incorporation assay ("FRET TDI"), dye-labeled oligonucleotide ligation assay ("DOL"), Taqman® with allele-specific oligonucleotides, randomly amplified polymorphic DNAs, and analysis by the Invader® (Third Wave Technologies) technique. Additional methods of polymorphism analysis are known to those of skill in the art. See, for example, Birren et al., supra.

In an embodiment of the invention, genetic polymorphism analysis can be carried out as described supra, in the apparatuses disclosed herein, which will thus be useful in these types of genetic analysis.

A method for SNP determination is by single base primer extension. In this technique, a primer is annealed to a polynucleotide that is to be tested for the presence of a SNP. The sequence of the primer is chosen such that the 3'-terminal nucleotide of the primer is adjacent to the site that is to be tested for the presence of the SNP. This template-primer complex is used for the preparation of four separate primer extension reactions, each containing only a single nucleotide. The reaction(s) in which extension occurs provides the sequence of the site being tested for the presence of the SNP. See, for example, U.S. Pat. No. 6,004,744.

Although extension can be assayed by DNA sequencing techniques, alternative assays are known in the art. One alternative assay for extension measures increases in molecular weight by mass spectroscopy, for example, matrix assisted laser desorption ionization time-of-flight (MALDI-TOF) spectrometry. Primers that have been extended by a single nucleotide, having a higher molecular weight, will be distinguished from unextended primers when analyzed by MALDI-TOF or other forms of mass spectrometry.

The apparatuses disclosed herein are useful in MALDI-TOF, and other types of mass spectrometric analyses, because transfer of extension products to a mass spectrometry preparation platform can be achieved by touching rather than pipetting. Consequently, multiple samples can be transferred simultaneously. Rapid sample preparation for multiple mass spectrophotometric analyses is accomplished by dehydration concentration of a sample on a hydrophilic region of an apparatus. The hydrophilic region can be located, for example, on the wall of a sample chamber.

The discovery of SNPs is efficiently accomplished by direct nucleotide sequence determination. The apparatuses disclosed herein provide an ideal route to SNP discovery by facilitating high-throughput nucleotide sequence determination.

Sandwiched Reactions

Chemical and biochemical reactions can be assembled by placing apparatuses containing individually pre-filled sample chambers adjacent to each other in such a way that corresponding samples in different apparatuses attain physical contact and the contents of the corresponding samples mix spontaneously. In one embodiment, the sample chambers in an apparatus are pre-loaded and allowed to dry so that the contents of the chambers (e.g., oligonucleotide primers) are in a state of dehydration. When such a dehydrated apparatus is brought into contact with an apparatus whose sample chambers are loaded with an aqueous reaction component, the dehydrated component(s) will be re-hydrated. This method can be practiced with several apparatuses at a time, allowing complex reactions to be assembled. A further advantage is that this method minimizes effects of evaporation that occur during reaction assembly, because all sample chambers are re-hydrated simultaneously when a stack of, for example, microhole arrays is assembled. Reactions can be conducted in a plurality of apparatuses arranged in a stacked or sandwiched configuration.

Addition of Reagents During Chemical Processing

Reagents can be added to reactions in progress in an apparatus, during incubation, by means of a piezo-electric dispenser or other common apparatus. In this way, the effects of evaporation can be countered by the addition of water; alternatively, chemicals and/or enzymes can be added to a reaction in progress. Using this method, reactions can be optimized as they proceed (i.e., in real-time).

Library Display and Assay

The apparatus of the invention can be used for creating and displaying libraries, for example, libraries of cells. For example, the sample chambers can comprise an adherent surface, suitable for cell growth, such as plastic, polystyrene and optionally polylysine. A different cell, cell strain or cell type can be applied to each sample chamber and the substrate placed under conditions suitable for cell growth; for example, the substrate is immersed in culture medium in a $CO_2$ incubator at 37° C. After a period of cell growth, the substrate is removed from the growth conditions and subjected to conditions that result in cell lysis and fixation of cellular macromolecules within or adjacent to the sample chambers. The substrate can then be subjected to, for example, restriction enzyme digestion, hybridization and/or amplification analysis to determine the presence of a particular target macromolecule in a particular cell, for example.

Real-Time Analysis of Reactions

Optical monitoring of the reactions contained in the sample chambers of the apparatus can be achieved in several ways. For example, an array of microholes containing a plurality of completed reactions can be placed in direct contact with a CCD array or fiber optics bundle, or can be loaded into an optical reading apparatus. For light-emitting readouts, such as fluorescence or chemiluminescence, a benefit of the microhole array is that there may be no plastic or other material to obscure or diffuse the emitted light and potentially generate autofluorescence. For thermal cycling reactions contained in a hydrophobic medium such as a bath of a hydrophobic substance, it is possible to monitor the optical activity of the reaction continuously. The hydrophobic substance itself can optically couple the reaction to a fiber optic bundle immersed in the hydrophobic substance which directs emitted light to a CCD array for quantitative detection. Such a device allows very high parallel processing of real-time assays such as PCR and Taqman®. Using fiber optic bundles capable of carrying hundreds of thousands to millions of individual fibers, it is possible to monitor millions of amplification reactions simultaneously and in real-time on a single apparatus such as a microhole plate.

High Throughput Sequencing

In addition to providing significant advantages in cycle sequencing, as described above, the use of the disclosed apparatuses, such as microhole arrays, for chemical reactions provides advantages in standard nucleotide sequencing operations as well. For example, it is possible to design a microhole sheet that is thin enough to fit between the glass plates of a standard polyacrylamide slab gel. The sheet has microholes arranged in a straight line array with each microhole containing a sub-microliter volume of a chain termination sequencing reaction. See, for example, FIG. 6A. The sheet is placed into a constant temperature or thermal cycling apparatus for processing of the sequencing reaction, and is then transferred to the top of a polyacrylamide gel or other electrophoresis medium, with one edge of the sheet contacting the electrophoresis medium. In one embodiment, the sheet contains partial holes along its perimeter into which reaction mixtures are dispensed and reactions are conducted, and from which reaction mixtures are applied directly to a gel by the method described above. A partial hole is one which is not completely enclosed by the substrate, such that up to about 180.degree. of the diameter of the hole is not enclosed by the substrate, i.e., up to 180.degree. of the hole diameter is open to the exterior of the substrate. See, for example, FIG. 6B. Alternatively, a hole can communicate with the exterior of the substrate through a thin channel in the substrate. See, for example, FIG. 6C.

For sequencing techniques in which the termination products corresponding to a particular one of the four nucleotides are labeled with a chromophore or fluorophore specific to that nucleotide, it is possible to combine the four base-specific reactions for analysis on a single gel lane. In this case, four arrays, each containing a different one of the four sequencing reactions in a corresponding hole, are stacked, and the stack is placed in contact with a sequencing gel such that the samples enter the gel upon provision of an electric current. Alternatively, the four plates are stacked so that the four sequencing reactions mix and the mixture equilibrates throughout the stack. Then one of the plates is removed from the stack and placed in contact with the gel.

Use of an apparatus such as a microhole sheet for gel loading has many advantages. The very small reaction sizes available with the sheets results in reduced reagent usage and consequent cost savings. Additionally, a sheet can be preloaded with hundreds of sequencing reactions, rather than the current limit of 96 samples per gel, thereby significantly expanding the capacity and throughput of current gel-based sequencing techniques and exceeding those of capillary sequencing instruments.

Additional Electrophoretic Applications

In another embodiment of the use of the disclosed apparatuses for electrophoresis, a microhole array containing a plurality of samples is placed such that one face of the array is in contact with an electrophoresis medium. In this way, several rows of samples can be simultaneously transferred to the electrophoretic medium to provide a three-dimensional electrophoretic analysis. Detection of samples during and/or after electrophoresis is accomplished, for example, by fluorescence. In one embodiment, a molecule which becomes fluorescent upon DNA binding (such as ethidium bromide, acridine orange or SYBR green, for example) is present in the electrophoretic medium. In another embodiment, the sample being subjected to analysis is labeled with a fluorescent molecule. In another embodiment, samples are radioactively labeled and detected with a radiation scanning device. In addition, they can be detected by silverstaining, Coomassie blue staining, and by binding of other proteins (e.g., antibodies).

In another embodiment, a stack of one or more gel- or liquid-filled microhole arrays can be formed to simulate an array of capillaries. An array containing a plurality of reactions can be placed upon the stack, and the reactions electrophoresed out of the array and into the stack. Subsequent to electrophoresis, the stack can be disassembled and the presence of a molecule in a particular array can be correlated with the position (level) of that array in the stack. The thickness of each array in the stack need not be uniform, although, in one embodiment, the stack comprises a plurality of arrays of uniform thickness. The holes in the stack can be filled with agarose, acrylamide, or any other medium suitable for electrophoresis. A similar stacking format can be used, for example, to conduct unit gravity sedimentation through a liquid.

Included within the embodiments of the invention are kits comprising the apparatus for containing multiple micro-volume liquid samples as described Supra. The kits may also comprise a component of a reaction to be carried-out in the apparatus; the component may be either a reactant or a reagent. In some embodiments, the reactant and/or reagent may be contained within one or more microholes of the apparatus. The kit may also contain in addition to the microhole apparatus, one or more hydrophobic substances to be used with the apparatus. The hydrophobic substances may be a hydrophobic fluid and/or a solid hydrophobic cover (e.g., a teflon porous membrane) and/or evaporation seals (e.g. optically clear silicone sheets). Additional contents of the kit may be a chamber for maintaining the appropriate environmental conditions, e.g., humidity and/or temperature, for the reaction(s) that are to be carried out using the microhole apparatus, and an apparatus(s) for loading the samples into the sample chambers. When the contents of the kit include a fluid substance, the fluid will be packaged in an appropriate container. Desirably, the kit will also contain instructions for use of the microhole apparatus.

The invention is further illustrated by the following non-limiting examples.

EXAMPLES

Example 1

PCR-mediated Analysis of CAG Repeat Length in the Human hSK Gene

A 10 ml aliquot of 2×PCR mastermix is prepared from commercially available components (e.g. GeneAmp® PCR Reagent Kit with AmpliTaq® DNA Polymerase; PE Biosystems, Foster City, Calif.) and custom oligonucleotide primers.

The master mix contains each of the following components at 1.6-times the desired final concentration:

```
Deoxynucleotides (dATP, dCTP, dGTP, TTP (or UTP))

A forward primer:
                                              (SEQ ID NO: 1)
FrwCAG2: GGA CCC TCG CTG CAG CCT CA A reverse primer:
                                              (SEQ ID NO: 2)
RewCAG2: GCA AGT GGT CAT TGA GAT TGA GCT GCC T
```

A thermostable DNA polymerase (e.g. AmpliTaq® DNA Polymerase)
A buffer
$MgCl_2$

Using a Hamilton 4000 robot, 1.7 µl of mastermix is dispensed into each of 576 microholes (24 rows and 24 columns) in a solid substrate (the microhole apparatus). The holes occur in the shape of a right circular cylinder of 1.2 mm diameter and 1.6 mm height. The microhole apparatus is suspended such that its lower face is shallowly immersed in mineral oil at a depth such that no mineral oil is forced into the microholes. Immediately following dispensing of the master mix, 1 µl of mineral oil is dispensed on top of each microhole.

Alternatively the apparatus is touched or immersed in a reservoir of master mix so that each microhole is filled with mastermix (internal volume of 1.7 µl). The apparatus is then shallowly immersed in mineral oil so that it is submerged to a depth of <1 mm.

Template DNA is prepared from blood or other tissue(s) from human patients of interest e.g., using QIAamp 96 DNA Blood BioRobot Kit (QIAGEN Inc., Valencia, Calif.). Using a Hamilton 4000 robot, 1 µl of DNA is removed from its position in a 96-well dish and is pipetted through the mineral oil into each microhole. Each microhole contains a distinct template DNA sample (derived from an individual patient) but each patient sample can be assayed multiple times in different microholes.

Following dispensing of the template DNA, the apparatus is immersed in a small volume (1-5 ml) of mineral oil. The mineral oil is thermally cycled as follows:

94° C. for 40 seconds, 4 cycles of (94° C. for 10 seconds, 70° C. for 50 seconds), and 28 cycles of (94° C. for 10 seconds, 68° C. for 50 seconds). After thermocycling, the substrate is removed from the oil bath and loading dye (which can contain bromphenol blue, xylene cyanole FF and/or Ficoll (commercially available from e.g., Bio101, Inc., Carlsbad, Calif.)) is dispensed into each microhole either using a Hamilton 4000 robot or by hand using an adjustable distance multichannel pipettor such as the Matrix Impact EXP. The material in the microholes is then aspirated and samples are dispensed into the wells of an 8% polyacrylamide gel and are electrophoresed to resolve differently sized products.

Example 2

Expression Analysis

Template mRNA (or total RNA) is prepared from the tissue(s) of human patients of interest e.g. using an RNeasy 96 BioRobot Kit (QIAGEN Inc., Valencia, Calif.). The RNA is combined with a mix containing reagents for reverse transcription and PCR amplification (e.g., GeneAmp® Gold RNA PCR Reagent Kit, PE Biosystems, Foster City, Calif.), excluding sequence-specific oligonucleotides and probes, such that the reagents are present at 1.6 times the desired final concentration. 1.7 µl of template/reagent mix is dispensed into each of 576 microholes in a microhole apparatus (the apparatus, as described above). Immediately following dispensing of the template, 1 µl of mineral oil is dispensed on top of each microhole.

Alternatively, the apparatus is touched or immersed in a reservoir of template RNA/reagent mix so that each microhole is filled with RNA/reagent mix (volume 1.7 µl). The substrate is then shallowly immersed in mineral oil so that it is submerged to a depth of <1 mm.

PCR primer/probe combinations corresponding to genes of interest are designed using e.g. Primer Express software (PE Biosystems, Foster City, Calif.). The fluorogenic probe for each sequence consists of an oligonucleotide with both reporter and quencher dye attached. Each probe anneals specifically between the forward and reverse amplification primers. When the probe is cleaved by the 5' nuclease activity of a DNA polymerase (e.g. AmpliTaq® DNA Polymerase; PE Biosystems, Foster City, Calif.), the reporter dye is separated from the quencher dye and a sequence-specific fluorescent signal is generated. The fluorescence intensity of the dye is proportional to the amount of starting material present in a patient sample.

Cognate PCR primers and probes corresponding to each gene of interest are mixed together at 2.7-fold the desired final concentration. 1 µl of each of the individual primer/probe mixes are dispensed into the microholes containing the RNA template/reagent mix using a Hamilton 4000 robot. Each microhole contains a distinct primer/probe combination (corresponding to an individual gene) but each gene can be assayed multiple times using different microholes.

Alternatively, primers and probes can be prepared at 2-fold the desired final concentration and can be dispensed into empty microholes of a separate apparatus. The primer and probe mixes are introduced into the RNA template/reagent mix by touching the two apparatuses together to allow mixing of the reagents.

Alternatively the desired amount of primers and probes can be dispensed into empty microholes, following which the apparatus is dessicated, allowing the primers/probe mix to dry onto the wall of each microhole. The entire apparatus is then touched or immersed in a reservoir of template RNA/reagent mix, so that each microhole is filled with RNA/reagent mix (volume 1.7 µl) as described above. The RNA/reagent mix rehydrates the desiccated primer/probe mix.

Following the introduction of template DNA, the substrate is immersed in a small volume (1-5 ml) of mineral oil. The mineral oil is thermally cycled as follows:

95° C. for 10 minutes, 20-40 cycles of (95° C. for 15 seconds, 60° C. for 60 seconds). After thermocycling, the apparatus is removed from the oil bath, covered on both sides with microscope slide coverslips and scanned on a confocal microscope. The substrate can be returned to the oil bath for additional cycling after scanning, if desired. Alternatively a device can be used to scan the reaction during each cycle of PCR while cycling is occurring.

Example 3

Figure 7:
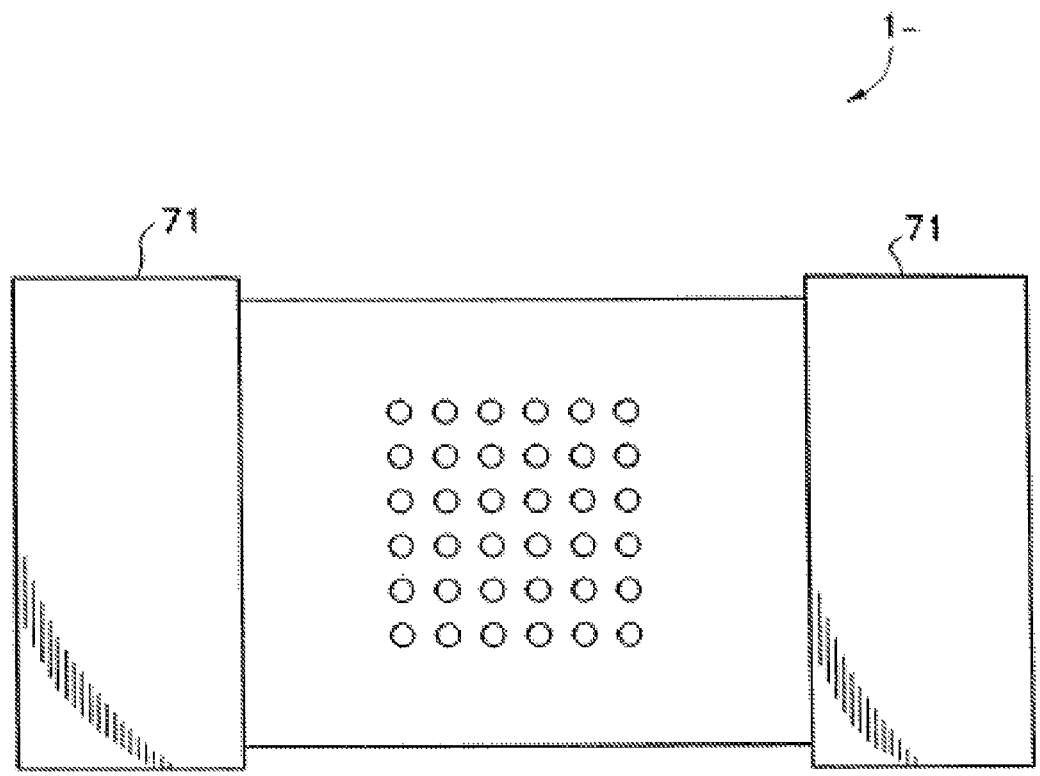
FIG. 7 is a top view of one embodiment of the claimed apparatus, wherein the apparatus is taped with aluminum tape.

Microhole PCR with Pre-Affixed Oligonucleotide Primers and In-Situ Fluorescent Detection PCR amplification of Lambda phage was performed in a microhole array with hole diameters of 1.0 mm and a titanium plate thickness of 1.1 mm. The titanium plate 1 was wrapped at the ends with aluminum tape 71 (FIG. 7) to ensure thermal contact of the plate to the heat block of a modified Perkin-Elmer 480 (PE480) thermal cycler while preventing physical contact between the heat block and the reactions contained in the holes. The PE480 thermal cycler was modified by cutting a channel across the width of the heater block to allow insertion and thermal cycling of microhole array plates. The channel was 2.4 mm wide, 18.8 mm deep and cut across the entire face of the heat block, a distance of 90 mm. The open ends of the channel were filled with heat conductive silicone caulk (Ultra Copper, Loctite Corporation, Rocky Hill, Conn.) and the cured assembly was filled with laboratory grade mineral oil (Sigma Chemical #M-5904).

Primers were designed to amplify a 632 by region of the Lambda DNA, forward primer=tggtatgaccggcatcct (SEQ ID NO: 3), reverse primer=tcggcgtgtcatatttcact (SEQ ID NO: 4). Initial loading of primer pairs onto the dried titanium microhole plate was 0.5 µl of 10 µmolar dilutions, giving 5 picomoles of forward and reverse primer in each well. The loaded reaction assembly was placed onto a 95° C. hot plate, the aluminum tape at the ends of the titanium plate providing a thermal path for increased evaporation rate while creating a standoff so that the loaded microholes would not make physical contact to the surface of the hot plate. After several minutes, the dried plate was removed.

A reaction mixture of 1 µl picogreen (Molecular Probes, Eugene, Oreg.), 1 ng Lambda Control DNA (AB Gene, Surrey, UK), 3 µl TE (pH=7.5), and 5 µl 2× master mix was prepared. The 2× master mix consisted of 10 µl 10× buffer concentration, 10 µl $MgCl_2$ (for a final concentration of 2.5 mM), 5 units RedTaq (Sigma Chemical #D-2812), 12 µl dNTPs (1.25 micromolar of each A,C,G,T). 0.5 µl of this reaction mixture was added to each of the holes in the microhole array, and thermal cycling was performed.

Thermal cycling parameters for the PE480 were as follows: 3 minutes at 95° C., 30 cycles of 95° C. for 30 secs, 55° C. for 30 secs, 73° C. for 60 sec, and 10 minutes at 72° C. After thermal cycling the microhole array was removed from the thermal cycler and placed on a confocal laser scanner/imager without removing the oil from the titanium substrate. The in-house imager/scanner uses a pair of coupled screw-drive robotic translation stages to scan the microhole array substrate in the x- and y-directions. An Argon-ion laser is focused through an objective lens onto the substrate, the excited emission returns through the objective lens and dichroic mirrors direct light of 530 nm(+/−20 nm) wavelength and 570 nm(+/−

20 nm) wavelength to two separate photomultiplier tubes (PMTs). The signal of the PMTs is collected and displayed on the attached computer.

The argon-ion laser excited the picogreen (which strongly fluoresces in the presence of double stranded DNA, but fluoresces only weakly in the presence of RNA and single stranded DNA) at 488 nm. A fluorescent signal from these reactions which is higher than pre-calibrated background signals indicates successful rehydration of the primers and amplification of the Lambda template.

Example 4

Molecular Haplotyping

Following the digital-PCR application outlined by Vogelstein and Kinzier (PNAS, vol. 96, p. 9236-9241), the microhole apparatuses described herein may be used to provide high confidence haplotype information. In this example we investigate the coincidence of a rare single base change which occurs in intron 34 of the ATM gene (IVS34-7 T>C) with a more common polymorphism which occurs in intron 48 of the same gene, an insertion of the three base sequence ATT (IVS48-69 insATT) (Thorstenson, Y R et al. American Journal of Human Genetics, vol. 69:396-412, 2001).

Samples of human DNA are prepared using the Stratagene DNA Extraction kit (CAT #200600, Stratagene, La Jolla, Calif.) according to manufacturer's instructions. The purified product is diluted to approximately 1.5 pg/µl to obtain a concentration of one-half genome equivalent DNA per 1 µl reaction.

A 256 hole microhole chip is used for this example. A 0.5 mm thick titanium plate with hole diameters of 0.75 mm will hold liquid samples of slightly less than 0.9 ul. 2500 of a PCR brew are prepared as follows: 67 mM Tris (pH 8.8), 16.6 mM NH4SO4, 10 mM 13-mercaptoethanol, 1 mM each A, C, G, T dNTPs, 6% (vol/vol) DMSO, 1 µM each forward and reverse primer, 11.1M each sequence probe (primers and probes described below), 12.5 U Platinum Taq (Life Technologies, Grand Island, N.Y.), and 125 genome equivalents of template DNA. Using a large bore 1-ml pipette, the reaction mixture is deposited on top of the horizontally held microhole array. The chip is re-oriented to be vertical, and the overflow liquid is carefully re-aspirated from each side of the chip using a 200-0 pipette. The top and bottom of the chip are sealed with a single sheet of clear adhesive film (such as parcel packaging tape) folded around one edge and sealed at the opposite edge with a face-to-face adhesive seal.

The assembly is inserted into a Perkin-Elmer 480 Thermal Cycler which has been modified by milling or sawing a narrow, deep groove across its face so that the thin microhole chip may be inserted into the groove and the chip reliably thermal cycled. A thin heat-conductive silicone pad (Stockwell Rubber Company, Philadelphia, Pa.) is used to provide thermal contact as well as pressure to the surfaces of the microhole chip. The added pressure prevents evaporation of the samples. The apparatus is thermal cycled according to the following protocol: (1) 94° C. for 60 sec; (2) 60 cycles of 94° C. for 20 sec, 55° C. for 20 sec, 70° C. for 20 sec; and (3) 70° C. for 10 minutes.

Following completion of the thermal cycling protocol the chip is scanned using a two color scanner or fluorescent microscope to determine the levels of fluorescence due to FAM (6-carboxy-fluorescein) (from exon 35) and TET (tetrachloro-6-carboxy-fluorescein) (from exon 49).

Of the 256 microholes, approximately 142 should have no fluorescent signal due to lack of DNA template. Of the remaining microholes, a FAM signal indicates the presence of the IVS34-7 T>C mutation of intron 34 and a TET signal indicates the presence of the IVS48-69 insATT mutation of intron 48. The case of a large number of FAM and TET signals from the same microholes indicates the very high likelihood that both mutations are present on the same allele. If both FAM and TET appear in the same microhole in only a few instances, this more likely indicates the presence in a single microhole of two different alleles.

Primers and Probes

The following primers are designed to amplify two specific loci on intron 34 and intron 48, separated by approximately 29 kb on the human ATM gene. The probes have been designed to hybridize to the polymorphic region (as opposed to the wild-type), therefore a FAM signal will be generated if intron 34 contains the T>C polymorphism and the TET signal will be generated if intron 48 contains an ATT insertion

|  | Primer Sequence |
|---|---|
| Intron | 34F: caaaagtgttgtcttcatgc (SEQ ID NO: 5) |
| Intron | 34R: ctgcaacaaattgacaact-agt (SEQ ID NO: 6) |
| Intron | 48F: taagatagtccctgacaagtagtta (SEQ ID NO: 7) |
| Intron | 48R: tgacatatgggaataaatactttt (SEQ ID NO: 8) |

Probe Sequences for Two Mutant Alleles of the ATM Gene (Mutations in Upper Case)

```
Intron
34Probe:
                                        (SEQ ID NO: 9)
<fam>tttaaaa<tamra>aattaCttctagataatcc-gca 31. Intron
48Probe:
                                        (SEQ ID NO: 10)
<tet>ttgctgc<tamra>tttcATT-attattattcat
```

Although the foregoing invention has been described in some detail by way of illustration and example for purposes of clarity of understanding, it will be apparent to those skilled in the art that various changes and modifications can be practiced without departing from the spirit of the invention. Therefore the foregoing descriptions and examples should not be construed as limiting the scope of the invention.

What is claimed:

1. A method for simultaneously conducting a plurality of polynucleotide reactions, the method comprising:
   (a) providing a microhole apparatus comprising a substrate having a first surface and a second surface and a plurality of holes extending through the substrate from the first surface to the second surface;
   (b) introducing a plurality of liquid samples comprising a nucleic acid into the plurality of holes;
   (c) coating the first surface, the second surface, and openings of the plurality of holes on the first and second surfaces of the apparatus with a hydrophobic fluid; and
   (d) placing the microhole apparatus with the coating of hydrophobic fluid into an environment favorable to simultaneously conducting a plurality of polynucleotide reactions on the plurality of liquid samples.

2. The method according to claim 1, wherein the polynucleotide reaction is a polynucleotide amplification reaction.

3. The method according to claim 1, wherein step (c) further comprises sealing the sample chambers with an evaporation barrier.

4. The method of claim 3, wherein the evaporation barrier consist of a silicone rubber sheet.

5. The method of claim 3, wherein the evaporation barrier consists of a polymeric or glass cover slide.

6. The method of claim 5, wherein the cover slide is optically clear.

7. The method according to claim 6, further comprising optically monitoring progress of the reactions in the chambers.

8. The method according to claim 7, wherein optically monitoring further comprises monitoring by fluorescence spectroscopy.

9. The method according to claim 1, wherein each hole or set of holes is circumscribed by a narrow raised feature.

10. The method according to claim 1, further comprising supplementing the reactions with one or more reagents during the course of the reactions.

11. The method according to claim 1, further comprising affixing a target nucleic acid to a wall of a hole by surface tension or desiccation.

12. The method according to claim 1, wherein the plurality of liquid samples is obtained from a single sample comprising the target nucleic acid sequence.

13. The method according to claim 12 wherein the single sample is a biological sample.

14. The method according to claim 1, wherein the microhole apparatus contains a sequence-specific polynucleotide amplification reaction component reversibly affixed to a wall of a hole.

15. The method according to claim 14, wherein the sequence-specific polynucleotide amplification reaction component is dissolved when the liquid sample is introduced into the hole.

16. The method according to claim 1, wherein the liquid samples are terminally diluted to the extent that an average number of the holes contain exactly one copy of the target nucleic acid.

17. The method according to claim 1, wherein haplotype information for a target nucleic acid sequence is generated.

18. The method according to claim 17, wherein a sequence-specific probe is used to detect a genetic polymorphism.

* * * * *